(12) United States Patent
Bourque et al.

(10) Patent No.: US 9,901,355 B2
(45) Date of Patent: Feb. 27, 2018

(54) TREPHINE

(75) Inventors: Bernard J. Bourque, Rehoboth, MA (US); Wei Li Fan, Malden, MA (US); Rebecca Ann Blough, West Warwick, RI (US); Ben Kim Graf, Madison, WI (US); William R. Davis, Hingham, MA (US)

(73) Assignee: Smith & Nephew, Inc., Memphis, TN (US)

(*) Notice: Subject to any disclaimer, the term of this patent is extended or adjusted under 35 U.S.C. 154(b) by 429 days.

(21) Appl. No.: 14/004,622

(22) PCT Filed: Mar. 12, 2012

(86) PCT No.: PCT/US2012/028803
§ 371 (c)(1),
(2), (4) Date: Feb. 26, 2014

(87) PCT Pub. No.: WO2012/125578
PCT Pub. Date: Sep. 20, 2012

(65) Prior Publication Data
US 2014/0309641 A1    Oct. 16, 2014

Related U.S. Application Data

(60) Provisional application No. 61/451,749, filed on Mar. 11, 2011, provisional application No. 61/451,751, filed on Mar. 11, 2011.

(51) Int. Cl.
A61B 17/16    (2006.01)
A61F 2/08     (2006.01)
(Continued)

(52) U.S. Cl.
CPC .......... *A61B 17/1635* (2013.01); *A61B 17/16* (2013.01); *A61B 17/1637* (2013.01);
(Continued)

(58) Field of Classification Search
CPC . A61B 17/16; A61B 17/1635; A61B 17/1637; A61B 17/1675; A61B 17/1697; A61F 2002/4645
See application file for complete search history.

(56) References Cited

U.S. PATENT DOCUMENTS

| 2,288,864 A | 7/1942 | Whitehead et al. |
| 3,316,795 A | 5/1967 | Tann |

(Continued)

FOREIGN PATENT DOCUMENTS

| CN | 2732211   | 10/2005 |
| CN | 1701772 A | 11/2005 |

(Continued)

OTHER PUBLICATIONS

Patent Examination Report No. 1 for related Australian Patent Application No. 2012267924 mailed Dec. 22, 2015.
(Continued)

*Primary Examiner* — Larry E Waggle, Jr.
(74) *Attorney, Agent, or Firm* — Norman F. Hainer, Jr.

(57) ABSTRACT

The present invention relates to medical apparatuses and procedures for reconstructing a ligament. There is provided a trephine (10) comprising an adaptor (11), an elongate reamer (12) coupled thereto, and a reamer support stem (13), wherein the reamer support stem is mounted concentrically within the reamer and adaptor, and wherein at least a portion of the reamer support stem is slidably moveable about a longitudinal axis of the trephine.

18 Claims, 17 Drawing Sheets

(51) Int. Cl.
*A61F 2/46* (2006.01)
*A61B 17/88* (2006.01)

(52) U.S. Cl.
CPC ...... *A61B 17/1675* (2013.01); *A61B 17/1697* (2013.01); *A61F 2/0805* (2013.01); *A61F 2/4644* (2013.01); *A61B 17/8897* (2013.01); *A61F 2002/0882* (2013.01); *A61F 2002/4645* (2013.01)

(56) References Cited

U.S. PATENT DOCUMENTS

| | | | |
|---|---|---|---|
| 3,320,783 A | 5/1967 | Kerr | |
| 3,499,222 A | 3/1970 | Linkow et al. | |
| 3,716,058 A | 2/1973 | Tanner | |
| 3,821,975 A | 7/1974 | Haker | |
| 3,869,942 A | 3/1975 | DeCaro | |
| 3,874,258 A | 4/1975 | Semola et al. | |
| 4,027,572 A | 6/1977 | Burge | |
| 4,177,797 A | 12/1979 | Baylis et al. | |
| 4,463,788 A | 8/1984 | Corona et al. | |
| D288,777 S | 3/1987 | Kwon | |
| 4,653,489 A | 3/1987 | Tronzo | |
| 4,738,255 A | 4/1988 | Goble et al. | |
| 4,741,651 A | 5/1988 | Despres | |
| 4,834,757 A | 5/1989 | Brantigan | |
| 4,854,311 A | 8/1989 | Steffee | |
| RE33,114 E | 11/1989 | Chiavon | |
| 4,913,143 A | 4/1990 | Oloff et al. | |
| 4,961,740 A | 10/1990 | Ray et al. | |
| 4,988,351 A | 1/1991 | Paulos et al. | |
| 5,026,373 A | 6/1991 | Ray et al. | |
| 5,055,104 A | 10/1991 | Ray | |
| 5,094,133 A | 3/1992 | Schreiber | |
| 5,116,337 A | 5/1992 | Johnson | |
| 5,129,904 A | 7/1992 | Illi | |
| 5,129,906 A | 7/1992 | Ross et al. | |
| 5,139,520 A | 8/1992 | Rosenberg | |
| 5,197,967 A * | 3/1993 | Wilson | A61B 17/1637 606/79 |
| 5,236,431 A | 8/1993 | Gogolewski et al. | |
| 5,242,447 A | 9/1993 | Borzone | |
| 5,312,214 A | 5/1994 | Morton | |
| 5,354,299 A | 10/1994 | Coleman | |
| 5,364,400 A | 11/1994 | Rego, Jr. et al. | |
| 5,370,662 A | 12/1994 | Stone et al. | |
| 5,383,878 A | 1/1995 | Roger et al. | |
| 5,407,427 A | 4/1995 | Zhu et al. | |
| 5,411,506 A | 5/1995 | Goble et al. | |
| 5,411,523 A | 5/1995 | Goble | |
| 5,423,823 A * | 6/1995 | Schmieding | A61F 2/08 606/179 |
| 5,431,660 A | 7/1995 | Burke | |
| 5,447,533 A | 9/1995 | Vachon et al. | |
| 5,464,427 A | 11/1995 | Curtis et al. | |
| 5,470,334 A | 11/1995 | Ross et al. | |
| 5,531,780 A | 7/1996 | Vachon | |
| 5,571,139 A | 11/1996 | Jenkins, Jr. | |
| 5,573,548 A | 11/1996 | Nazre et al. | |
| 5,593,409 A | 1/1997 | Michelson | |
| 5,609,635 A | 3/1997 | Michelson | |
| 5,609,636 A | 3/1997 | Kohrs et al. | |
| 5,626,613 A | 5/1997 | Schmieding | |
| 5,632,747 A * | 5/1997 | Scarborough | A61B 17/1637 408/209 |
| 5,645,547 A | 7/1997 | Coleman | |
| 5,658,285 A | 8/1997 | Marnay et al. | |
| 5,676,545 A | 10/1997 | Jones | |
| 5,681,352 A | 10/1997 | Clancy, III et al. | |
| 5,688,285 A | 11/1997 | Yamada | |
| 5,690,676 A | 11/1997 | Dipoto et al. | |
| 5,695,497 A | 12/1997 | Stahelin | |
| 5,702,397 A | 12/1997 | Goble et al. | |
| 5,709,683 A | 1/1998 | Bagby | |
| 5,802,794 A | 9/1998 | Robson | |
| 5,833,715 A | 11/1998 | Vachon et al. | |
| 5,876,405 A * | 3/1999 | Del Rio | A61B 17/1695 606/80 |
| 5,888,227 A | 3/1999 | Cottle | |
| 5,891,146 A | 4/1999 | Simon et al. | |
| 5,921,982 A | 7/1999 | Lesh et al. | |
| 5,951,560 A | 9/1999 | Simon et al. | |
| 5,961,524 A | 10/1999 | Crombie | |
| 5,964,783 A | 10/1999 | Grafton et al. | |
| 5,968,047 A | 10/1999 | Reed | |
| 5,968,098 A | 10/1999 | Winslow | |
| 5,984,967 A | 11/1999 | Zdeblick et al. | |
| 6,008,433 A | 12/1999 | Stone | |
| 6,039,762 A | 3/2000 | McKay | |
| 6,086,593 A | 7/2000 | Bonutti | |
| 6,096,060 A | 8/2000 | Fitts et al. | |
| 6,097,986 A | 8/2000 | Janke et al. | |
| 6,132,435 A | 10/2000 | Young | |
| 6,146,073 A | 11/2000 | Kobusch | |
| 6,196,780 B1 | 3/2001 | Wakai et al. | |
| 6,214,031 B1 | 4/2001 | Schmieding et al. | |
| 6,216,348 B1 | 4/2001 | Martirossian | |
| 6,235,057 B1 | 5/2001 | Roger et al. | |
| 6,283,973 B1 | 9/2001 | Hubbard et al. | |
| 6,302,632 B1 | 10/2001 | Lin | |
| 6,360,129 B1 | 3/2002 | Ley et al. | |
| 6,443,989 B1 | 9/2002 | Jackson | |
| 6,447,545 B1 | 9/2002 | Bagby | |
| 6,488,683 B2 | 12/2002 | Lieberman | |
| 6,503,251 B1 | 1/2003 | Shadduck | |
| 6,511,499 B2 | 1/2003 | Schmieding et al. | |
| 6,514,257 B2 | 2/2003 | Dovesi et al. | |
| 6,517,542 B1 | 2/2003 | Papay et al. | |
| 6,527,774 B2 | 3/2003 | Lieberman | |
| 6,544,265 B2 | 4/2003 | Lieberman | |
| 6,551,319 B2 | 4/2003 | Lieberman | |
| 6,551,320 B2 | 4/2003 | Lieberman | |
| 6,551,322 B1 | 4/2003 | Lieberman | |
| 6,554,830 B1 | 4/2003 | Chappius | |
| 6,589,245 B1 | 7/2003 | Weiler et al. | |
| 6,604,945 B1 | 8/2003 | Jones | |
| 6,626,917 B1 | 9/2003 | Craig | |
| 6,648,903 B1 | 11/2003 | Pierson | |
| 6,656,183 B2 | 12/2003 | Colleran et al. | |
| 6,666,888 B1 | 12/2003 | Jackson | |
| 6,685,728 B2 | 2/2004 | Sinnott et al. | |
| 6,818,010 B2 | 11/2004 | Eichhorn et al. | |
| 6,823,871 B2 | 11/2004 | Schmieding | |
| 6,855,168 B2 | 2/2005 | Crozet | |
| 6,857,343 B1 | 2/2005 | Easterbrooks et al. | |
| 6,863,671 B1 | 3/2005 | Strobel et al. | |
| 6,942,669 B2 * | 9/2005 | Kurc | A61B 17/1635 606/80 |
| 6,953,462 B2 | 10/2005 | Lieberman | |
| 7,033,372 B1 | 4/2006 | Cahalan | |
| 7,070,586 B2 | 7/2006 | Hart et al. | |
| 7,083,647 B1 | 8/2006 | Sklar et al. | |
| 7,090,690 B2 | 8/2006 | Foerster et al. | |
| 7,147,641 B2 | 12/2006 | Chen | |
| 7,189,251 B2 | 3/2007 | Kay | |
| 7,195,634 B2 | 3/2007 | Schmieding et al. | |
| 7,217,279 B2 | 5/2007 | Reese | |
| 7,322,978 B2 | 1/2008 | West | |
| 7,322,986 B2 | 1/2008 | Wolf | |
| 7,335,221 B2 | 2/2008 | Collier et al. | |
| 7,371,244 B2 | 5/2008 | Chatlynne et al. | |
| 7,572,264 B2 | 8/2009 | Null et al. | |
| 7,575,572 B2 | 8/2009 | Sweeney | |
| 7,585,311 B2 | 9/2009 | Green et al. | |
| 7,594,929 B2 | 9/2009 | Collette | |
| 7,608,098 B1 | 10/2009 | Stone et al. | |
| 7,867,252 B2 | 1/2011 | Criscuolo et al. | |
| 7,883,529 B2 | 2/2011 | Sinnott et al. | |
| 7,896,902 B2 | 3/2011 | Jeon et al. | |
| 7,914,539 B2 | 3/2011 | Stone et al. | |
| 7,935,138 B1 | 5/2011 | Richelsoph | |
| 7,993,369 B2 | 8/2011 | Dreyfuss et al. | |
| 8,016,865 B2 | 9/2011 | Donnelly et al. | |
| 8,034,090 B2 | 10/2011 | Stone et al. | |

(56) References Cited

U.S. PATENT DOCUMENTS

| | | |
|---|---|---|
| 8,167,906 B2 | 5/2012 | Cauldwell et al. |
| 8,343,186 B2 | 1/2013 | Dreyfuss et al. |
| 8,372,124 B2 | 2/2013 | Paulk et al. |
| 8,430,909 B2 | 4/2013 | Dreyfuss et al. |
| 8,480,686 B2 | 7/2013 | Bakos et al. |
| 8,597,328 B2 | 12/2013 | Cauldwell et al. |
| 8,623,049 B2 | 1/2014 | Ward |
| 8,623,052 B2 | 1/2014 | Dreyfuss et al. |
| 8,636,799 B2 | 1/2014 | Sklar et al. |
| 8,672,967 B2 | 3/2014 | DiMatteo et al. |
| 8,715,282 B2 | 5/2014 | Pool |
| 8,801,755 B2 | 8/2014 | Dreyfuss et al. |
| 8,821,541 B2 | 9/2014 | Dreyfuss et al. |
| 8,900,279 B2 | 12/2014 | Assell et al. |
| 8,974,505 B2 | 3/2015 | Sawa et al. |
| 8,979,848 B2 | 3/2015 | Butters et al. |
| 8,979,865 B2 | 3/2015 | Fan et al. |
| 9,155,531 B2 | 10/2015 | Housman |
| 9,162,350 B2 | 10/2015 | Nino et al. |
| 9,237,887 B2 | 1/2016 | Wack et al. |
| 9,277,911 B2 | 3/2016 | Hernandez |
| 9,308,080 B2 | 4/2016 | Housman et al. |
| 9,393,006 B2 | 7/2016 | Housman et al. |
| 9,427,270 B2 | 8/2016 | Housman |
| 9,526,488 B2 | 12/2016 | Arai et al. |
| 9,579,188 B2 | 2/2017 | Bowman et al. |
| 2002/0022862 A1 | 2/2002 | Grafton et al. |
| 2002/0052629 A1 | 5/2002 | Morgan et al. |
| 2002/0055737 A1 | 5/2002 | Lieberman |
| 2002/0055738 A1 | 5/2002 | Lieberman |
| 2002/0055742 A1 | 5/2002 | Lieberman |
| 2002/0087189 A1 | 7/2002 | Bonutti |
| 2002/0087190 A1 | 7/2002 | Benavitz et al. |
| 2002/0099382 A1 | 7/2002 | Salazar et al. |
| 2002/0111653 A1 | 8/2002 | Foerster |
| 2002/0143335 A1 | 10/2002 | von Hoffmann et al. |
| 2002/0165546 A1 | 11/2002 | Goble et al. |
| 2003/0055431 A1 | 3/2003 | Brannon |
| 2003/0065361 A1 | 4/2003 | Dreyfuss |
| 2003/0065374 A1 | 4/2003 | Honeck |
| 2003/0069640 A1 | 4/2003 | Ferreira et al. |
| 2003/0078585 A1 | 4/2003 | Johnson et al. |
| 2003/0125749 A1 | 7/2003 | Yuan et al. |
| 2003/0181913 A1 | 9/2003 | Lieberman |
| 2003/0195529 A1 | 10/2003 | Takamoto et al. |
| 2004/0015170 A1 | 1/2004 | Tallarida et al. |
| 2004/0030343 A1 | 2/2004 | Kurc |
| 2004/0039404 A1 | 2/2004 | Dreyfuss |
| 2004/0073216 A1 | 4/2004 | Lieberman |
| 2004/0093032 A1 | 5/2004 | Sinnott et al. |
| 2004/0097945 A1 | 5/2004 | Wolf |
| 2004/0122424 A1 | 6/2004 | Ferree |
| 2004/0143158 A1 | 7/2004 | Hart et al. |
| 2004/0143237 A1 | 7/2004 | Hart et al. |
| 2004/0153074 A1 | 8/2004 | Bojarski et al. |
| 2004/0267265 A1 | 12/2004 | Kyle |
| 2005/0107828 A1 | 5/2005 | Reese |
| 2005/0159727 A1 | 7/2005 | Lesh |
| 2005/0222681 A1 | 10/2005 | Richley et al. |
| 2005/0234458 A1 | 10/2005 | Huebner |
| 2005/0250984 A1 | 11/2005 | Lam et al. |
| 2005/0250985 A1 | 11/2005 | Saadat et al. |
| 2005/0250987 A1 | 11/2005 | Ewers et al. |
| 2005/0250988 A1 | 11/2005 | Ewers et al. |
| 2005/0267478 A1 | 12/2005 | Corradi et al. |
| 2005/0283239 A1 | 12/2005 | Crozet |
| 2006/0009769 A1 | 1/2006 | Lieberman |
| 2006/0030948 A1 | 2/2006 | Manrique et al. |
| 2006/0079895 A1 | 4/2006 | McLeer |
| 2006/0079903 A1 | 4/2006 | Wong |
| 2006/0089651 A1 | 4/2006 | Trudeau et al. |
| 2006/0100627 A1 | 5/2006 | Stone et al. |
| 2006/0106390 A1 | 5/2006 | Jensen et al. |
| 2006/0142769 A1 | 6/2006 | Collette |
| 2006/0149266 A1 | 7/2006 | Cordasco |
| 2006/0217681 A1 | 9/2006 | Hart et al. |
| 2006/0241636 A1 | 10/2006 | Novak et al. |
| 2006/0247642 A1 | 11/2006 | Stone et al. |
| 2006/0253080 A1 | 11/2006 | Tulleken et al. |
| 2006/0276841 A1 | 12/2006 | Barbieri et al. |
| 2007/0032797 A1 | 2/2007 | Ortiz et al. |
| 2007/0093895 A1 | 4/2007 | Donnelly et al. |
| 2007/0122764 A1 | 5/2007 | Balfour et al. |
| 2007/0142849 A1 | 6/2007 | Ewers et al. |
| 2007/0185532 A1 | 8/2007 | Stone et al. |
| 2007/0198019 A1 | 8/2007 | Schomer et al. |
| 2007/0203498 A1 | 8/2007 | Gerber et al. |
| 2008/0027446 A1 | 1/2008 | Stone et al. |
| 2008/0065114 A1 | 3/2008 | Stone et al. |
| 2008/0082128 A1 | 4/2008 | Stone |
| 2008/0132932 A1 | 6/2008 | Hoeppner |
| 2008/0140092 A1 | 6/2008 | Stone et al. |
| 2008/0140093 A1 | 6/2008 | Stone et al. |
| 2008/0154314 A1 | 6/2008 | McDevitt |
| 2008/0179839 A1 | 7/2008 | Walters |
| 2008/0275431 A1 | 11/2008 | Stone et al. |
| 2009/0024174 A1 | 1/2009 | Stark |
| 2009/0042951 A1 | 2/2009 | Danziger |
| 2009/0076544 A1 | 3/2009 | DiMatteo et al. |
| 2009/0118776 A1 | 5/2009 | Kelsch et al. |
| 2009/0125071 A1 | 5/2009 | Skinlo et al. |
| 2009/0187216 A1 | 7/2009 | Schmieding et al. |
| 2009/0248029 A1 | 10/2009 | Paulos |
| 2009/0292321 A1 | 11/2009 | Collette |
| 2009/0319043 A1 | 12/2009 | McDevitt et al. |
| 2010/0094297 A1 | 4/2010 | Parmigiani |
| 2010/0094352 A1 | 4/2010 | Iott et al. |
| 2010/0106166 A1 | 4/2010 | Cropper et al. |
| 2010/0274298 A1 | 10/2010 | Schiff |
| 2011/0054526 A1 | 3/2011 | Stone et al. |
| 2011/0112576 A1 | 5/2011 | Nguyen et al. |
| 2011/0130760 A1 | 6/2011 | Anderson et al. |
| 2011/0213426 A1 | 9/2011 | Yedlicka et al. |
| 2011/0224727 A1 | 9/2011 | Housman et al. |
| 2011/0282450 A1 | 11/2011 | Donnelly et al. |
| 2011/0319933 A1 | 12/2011 | Tepic |
| 2012/0041448 A1 | 2/2012 | Schumacher et al. |
| 2012/0059384 A1 | 3/2012 | Fan et al. |
| 2012/0179163 A1 | 7/2012 | Housman et al. |
| 2012/0330420 A1 | 12/2012 | Brodke et al. |
| 2013/0150859 A1 | 6/2013 | Kehres et al. |
| 2013/0158596 A1 | 6/2013 | Miller et al. |
| 2013/0158597 A1 | 6/2013 | Hernandez |
| 2013/0158598 A1 | 6/2013 | Lizardi |
| 2013/0158599 A1 | 6/2013 | Hester et al. |
| 2013/0158610 A1 | 6/2013 | Hernandez |
| 2013/0178901 A1 | 7/2013 | Arai et al. |
| 2014/0081339 A1 | 3/2014 | Bowman et al. |
| 2014/0142697 A1 | 5/2014 | Sklar et al. |
| 2014/0148850 A1 | 5/2014 | DiMatteo et al. |
| 2014/0172016 A1 | 6/2014 | Housman |
| 2014/0277129 A1 | 9/2014 | Arai et al. |
| 2014/0277130 A1 | 9/2014 | Housman |
| 2014/0277188 A1 | 9/2014 | Poulos |
| 2014/0277192 A1 | 9/2014 | Housman |
| 2015/0196388 A1 | 7/2015 | Housman et al. |
| 2015/0327984 A1 | 11/2015 | Arai et al. |
| 2016/0235399 A1 | 8/2016 | Housman et al. |
| 2016/0374661 A1 | 12/2016 | Housman et al. |
| 2017/0014224 A1 | 1/2017 | Arai et al. |
| 2017/0020589 A1 | 1/2017 | Bowman et al. |
| 2017/0049438 A1 | 2/2017 | Arai et al. |

FOREIGN PATENT DOCUMENTS

| | | |
|---|---|---|
| CN | 1829479 A | 9/2006 |
| CN | 101002703 | 7/2007 |
| CN | 101031248 A | 9/2007 |
| CN | 101422381 A | 5/2009 |
| CN | 101573078 A | 11/2009 |
| CN | 201436022 U | 4/2010 |
| CN | 102068305 A | 5/2011 |
| CN | 102475586 | 5/2012 |
| CN | 102512253 A | 6/2012 |

(56) References Cited

FOREIGN PATENT DOCUMENTS

| | | |
|---|---|---|
| CN | 102525580 | 7/2012 |
| CN | 102525583 A | 7/2012 |
| CN | 102551821 A | 7/2012 |
| CN | 102781370 | 11/2012 |
| CN | 102905636 A | 1/2013 |
| CN | 102573662 B | 8/2015 |
| EP | 05202698 A1 | 9/1992 |
| EP | 0538895 A2 | 4/1993 |
| EP | 0682917 B1 | 11/1995 |
| EP | 0686373 A1 | 12/1995 |
| EP | 0502698 B1 | 11/1997 |
| EP | 0669110 B1 | 5/2000 |
| EP | 1147751 B1 | 10/2001 |
| EP | 1093774 B1 | 6/2002 |
| EP | 1234637 A2 | 8/2002 |
| EP | 0796593 B1 | 5/2004 |
| EP | 1430843 A2 | 6/2004 |
| EP | 1917926 A1 | 5/2008 |
| EP | 2036501 A3 | 3/2009 |
| EP | 2422711 A2 | 2/2012 |
| EP | 2422712 A1 | 2/2012 |
| EP | 2422712 A2 | 2/2012 |
| EP | 2596758 A1 | 5/2013 |
| EP | 2601894 A1 | 6/2013 |
| FR | 2760355 A1 | 9/1998 |
| FR | 2803739 A1 | 7/2001 |
| FR | 2846867 A1 | 5/2004 |
| FR | 2879915 A1 | 6/2006 |
| GB | 2294399 A | 5/1996 |
| JP | H10-000200 | 1/1998 |
| JP | H10200 A | 1/1998 |
| JP | 2005-529650 | 10/2005 |
| JP | 2005529650 | 10/2005 |
| JP | 2006212449 A | 8/2006 |
| JP | 2006-305348 A | 11/2006 |
| WO | 9608205 A1 | 3/1996 |
| WO | 9619947 A1 | 7/1996 |
| WO | 9802117 A1 | 1/1998 |
| WO | 9826717 A1 | 6/1998 |
| WO | 03063713 A1 | 8/2003 |
| WO | 20030063713 | 8/2003 |
| WO | 03103507 A2 | 12/2003 |
| WO | 2006055516 A2 | 5/2006 |
| WO | 2007/093192 A1 | 8/2007 |
| WO | 2007093192 A1 | 8/2007 |
| WO | 2008021474 A2 | 2/2008 |
| WO | 2008100944 A1 | 8/2008 |
| WO | 2008100994 A1 | 8/2008 |
| WO | 2009042951 A1 | 4/2009 |
| WO | 2010017631 A1 | 2/2010 |
| WO | 20100017584 | 2/2010 |
| WO | 2010053708 A1 | 5/2010 |
| WO | 2011059995 A2 | 5/2011 |
| WO | 2011060022 A2 | 5/2011 |
| WO | 2011112776 A1 | 9/2011 |
| WO | 20110112576 | 9/2011 |
| WO | 20120129388 | 9/2012 |
| WO | 2012171011 A1 | 12/2012 |
| WO | 2010009217 A1 | 9/2015 |

OTHER PUBLICATIONS

Hunt, Patrick, D.V.M. et al. "Development of a Perforated Biodegradable Interference Screw", Arthroscopy: The Journal of Arthroscopic and Related Surgery, vol. 21, No. 3, Mar. 2005; pp. 258-265.
International Search and Written Opinion for PCT/US2011/027837 mailed May 19, 2011.
Smith & Nephew brochure titled "Bio RCITM Bioabsorbable Screws: Anatomically Targeted Screws for ACL and PCL Reconstruction", 2000.
Biomet brochure "Bio-CoreTM Interference Screw", 2007.
International Search and Written Opinion for PCT/US2009/065304 mailed Jun. 5, 2013.
International Search and Written Opinion for PCT/US2012/041298 mailed Jun. 5, 2013.
Second Office Action for Chinese Patent Application No. 200980155954.7, issued Oct. 24, 2013.
Notice of Reasons for Rejections for Japanese Patent Application No. 2011-538642, mailed Oct. 1, 2013.
First Office Action for Chinese Patent Application No. 200980155954.7, issued Apr. 12, 2013.
Communication from related European Patent Application No. 09761114.9 mailed Dec. 3, 2015.
Communication from related European Patent Application No. 11710940.5 mailed Dec. 8, 2015.
First Office Action for related Chinese Patent Application No. 201280038677.3 issued Sep. 6, 2015.
Decision of Rejection on related Japanese Patent Application No. 2012-557236 mailed Oct. 9, 2015.
International Preliminary Report on Patentability for related International Application No. PCT/US2014/033535, mailed Oct. 22, 2015.
Third Office Action for related Chinese Patent Application No. 2011-80013194.3 issued Aug. 21, 2015.
Notice of Reasons for Rejection for Japanese Patent Application No. 2012-557236 mailed Mar. 2, 2015.
First Office Action for Chinese Patent Application No. 201180013194.3, issued Jul. 21, 2014.
International Search and Written Opinion for PCT/US2014/033535 mailed Jul. 18, 2014.
International Search and Written Opinion for PCT/US2014/022539 mailed Jun. 27, 2014.
International Search and Written Opinion for PCT/US2014/020747 mailed Jun. 6, 2014.
Decision of Rejections for Japanese Patent Application No. 2011-538642, mailed Jun. 2, 2014.
Second Office Action for related Chinese Patent Application No. 201280022627.6 issued Sep. 16, 2015.
Substantive Examination for related Mexican Patent Application No. MX/a/2013/010383 issued Aug. 12, 2015.
Patent Examination Report No. 1 for related Australian Patent Application No. 2012229152 Issued Aug. 18, 2015.
International Search and Written Opinion for PCT/US2014/066389 mailed Feb. 17, 2015.
Patent Examination Report No. 1 for Australian Patent Application No. 2011224326 issued Apr. 21, 2015.
Second Office Action for Chinese Patent Application No. 201180013194.3, issued Mar. 23, 2015.
First Office Action for Chinese Patent Application No. 201280022627.6, issued Apr. 13, 2015.
Notice of Reasons for Rejection for Japanese Patent Application No. 2012-557236 mailed Nov. 25, 2014.
Patent Examination Report No. 1 for Australian Patent Application No. 2009319879 issued Nov. 10, 2014.
Substantive Examination Report from related Mexico Patent Application No. MX/a/2013/010383 mailed Jan. 19, 2016.
Notice of Reasons for Rejection for related Japanese Application No. 2013-558094 mailed Feb. 2, 2016.
Substantive Examination of related Russian Application No. 2013144961/14(069526) mailed Dec. 23, 2015.
Second Office Action from related Chinese Application No. 201280038677.3 issued May 5, 2016.
International Preliminary Report on Patentability from related PCT Application No. PCT/US2014/066389 issued May 24, 2016.
Office Action from related Mexican Application No. MX/a/2013/010383 issued May 3, 2016.
Notice of Reasons for Rejection from related Japanese Application No. 2014-514625 issued Jun. 13, 2016.
Communication from EPO from related European Application No. 12711719.0-1666 issued Jul. 28, 2016.
Third Office Action from related Chines Application No. 201280022627.6 issued Mar. 4, 2016.
Office Action and Search Report from related Chinese Application No. 201480032876.2 issued Oct. 19, 2016.
First Office Action from related Chinese Application No. 201480012203.0 issued Aug. 17, 2016.

(56) References Cited

OTHER PUBLICATIONS

Office Action from related Japanese Application No. 2013-558094 issued Sep. 5, 2016.
Office Action from related Russian Application No. 2015147534/20(073143) issued Jun. 29, 2016.
Office Communication from related European Application No. 14712930.8-1662 issued Nov. 24, 2016.
Office Action from related Chinese Application No. 201280038677.3 issued Nov. 28, 2016.
Office Action from related Japanese Application No. 2014-514625 issued Dec. 19, 2016.
Office Action from related Russian Application No. 2016124173/20(037886) dated Jan. 19, 2017.
Office Action from related EPO Application No. 14716107.9—1664 dated Mar. 23, 2017.
Communication from related European Application No. 14724272.1—1664 dated Jun. 13, 2017.
Second Office Action from related Chinese Application No. 201480012203.0 dated Apr. 24, 2017.
First Office Action for Chinese Patent Application No. 201480073698.8 dated May 2, 2017.
First Office Action from related Chinese Application No. 201480014353.5 dated Apr. 19, 2017.
Fourth Office Action from related Chinese Application No. 201280038677.3 dated May 26, 2017.
Second Office Action from related Chinese Application No. 201480032876.2 dated May 31, 2017.

\* cited by examiner

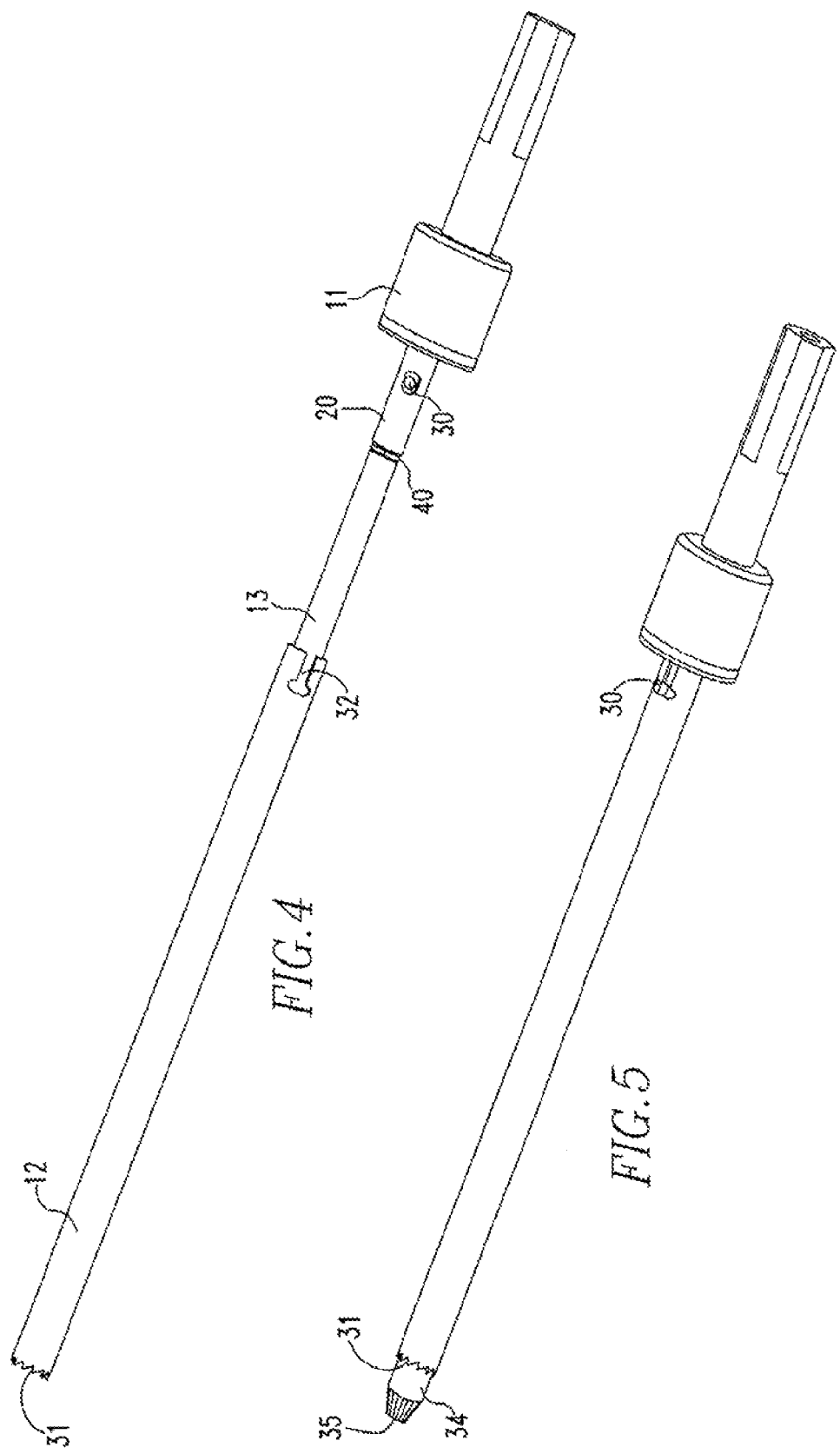

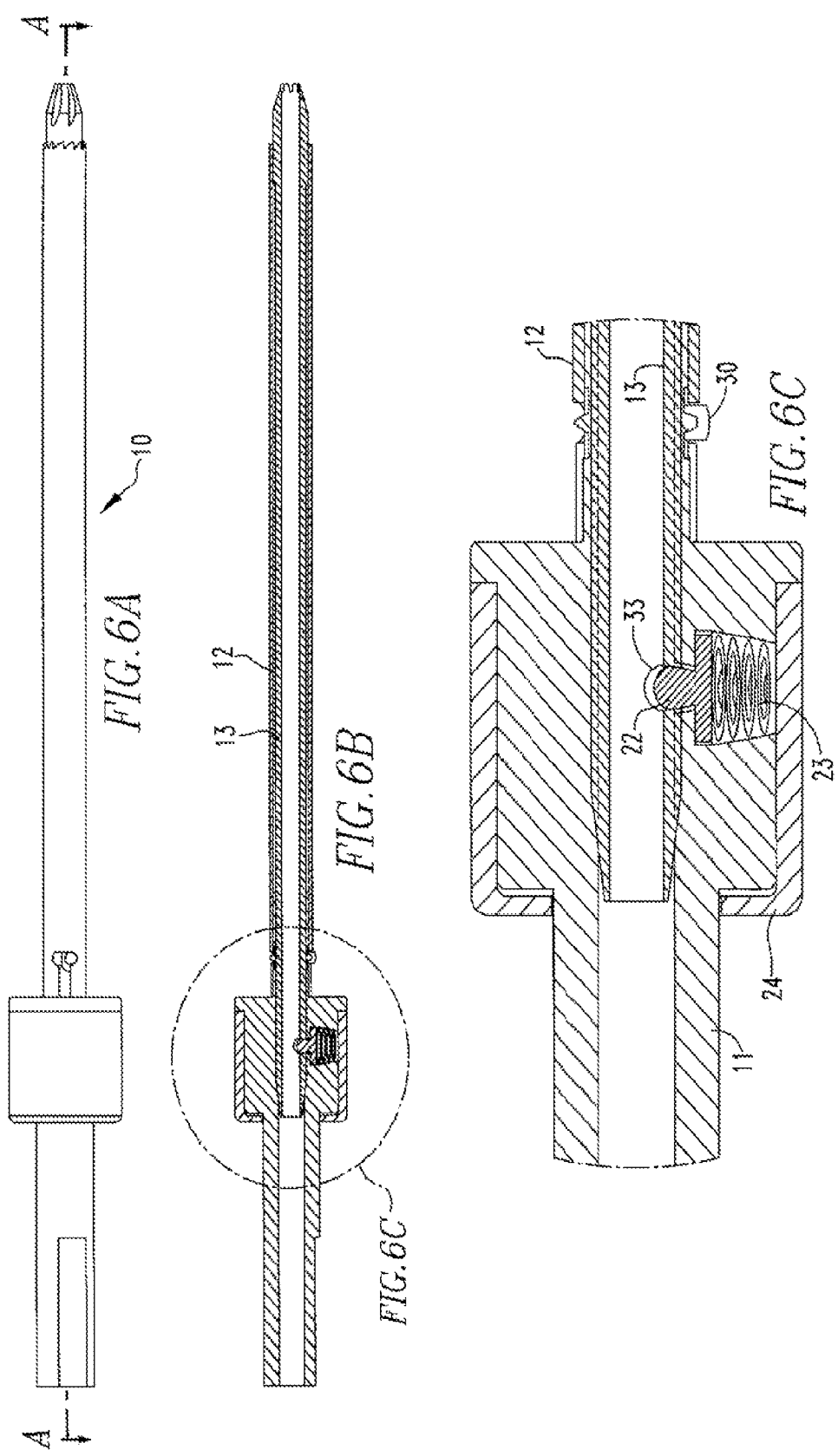

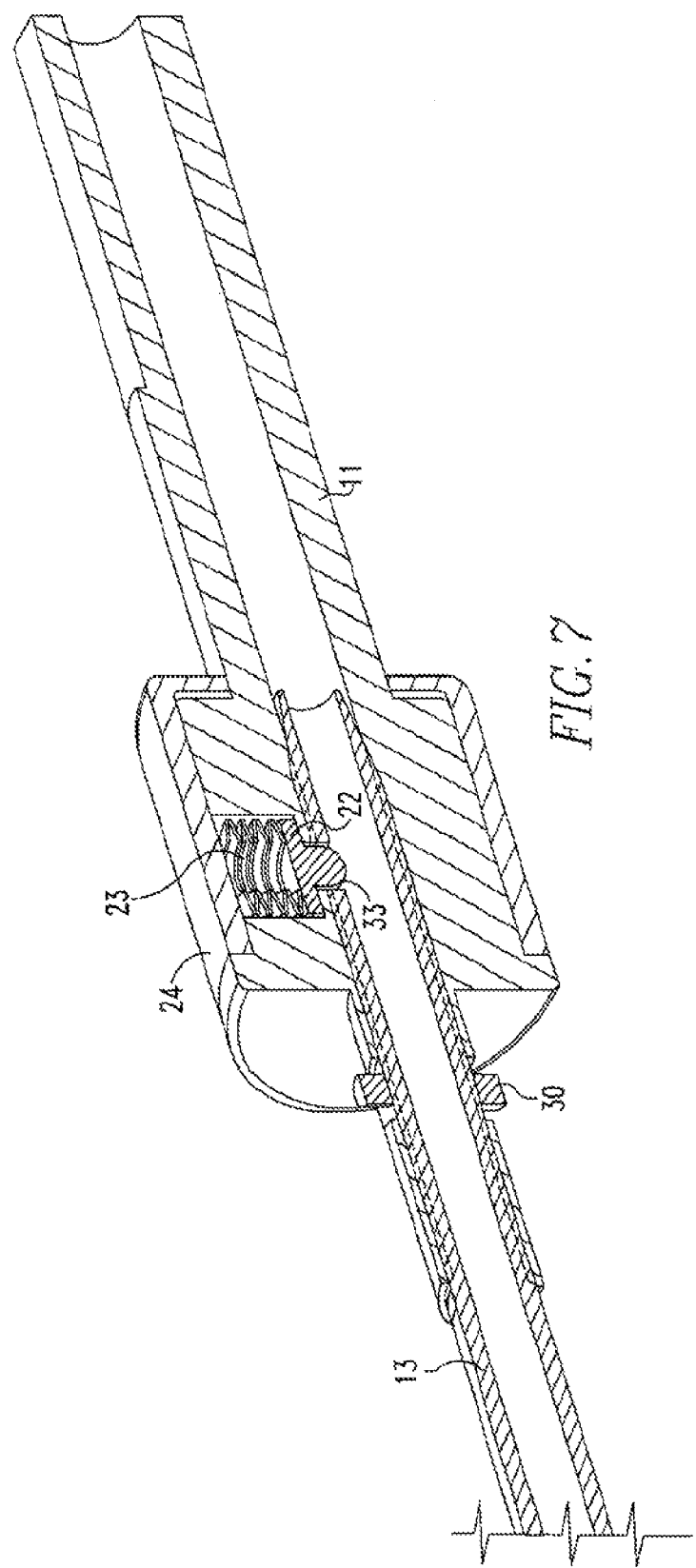

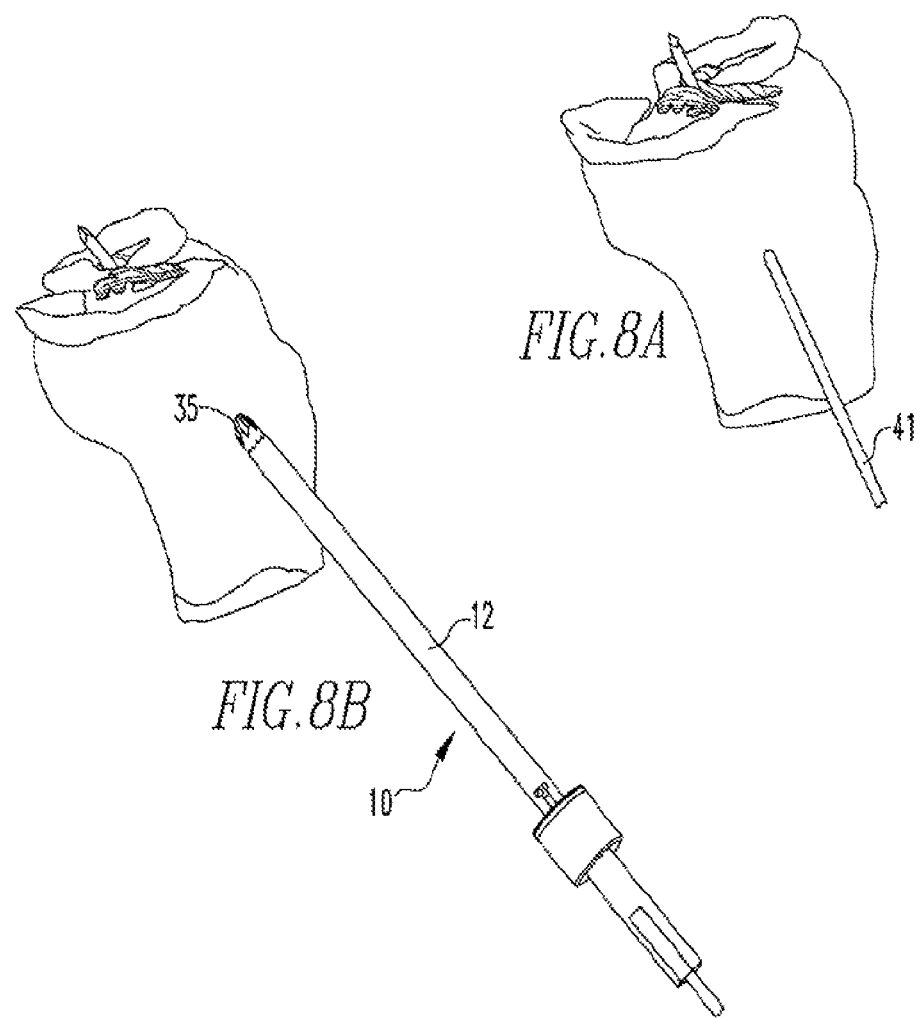
FIG.8A
FIG.8B
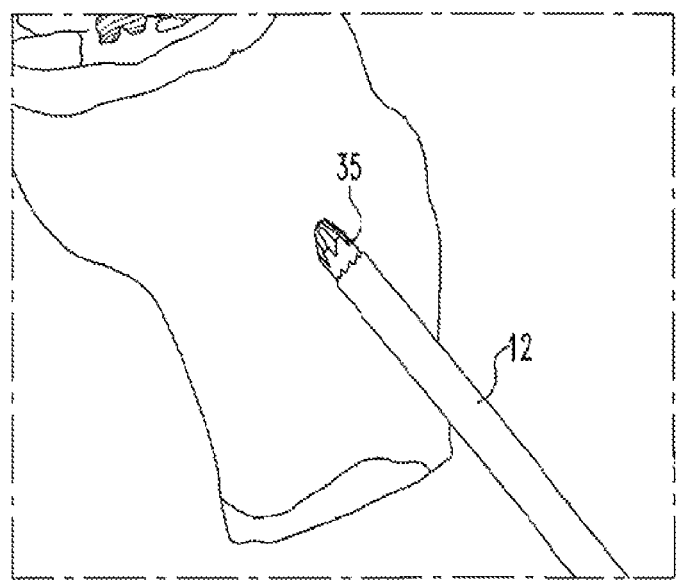
FIG.8C

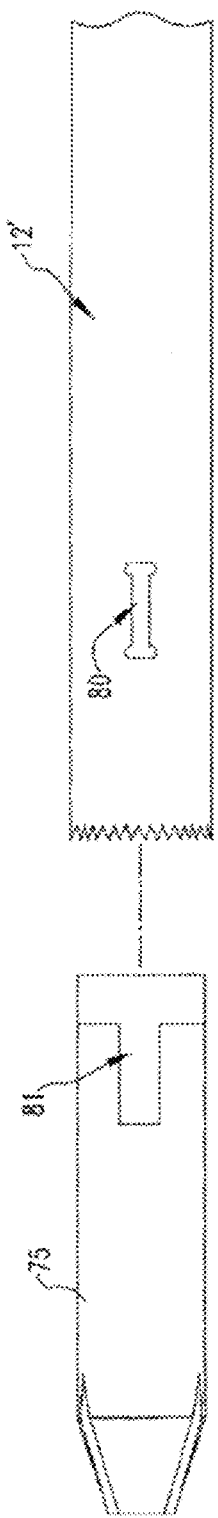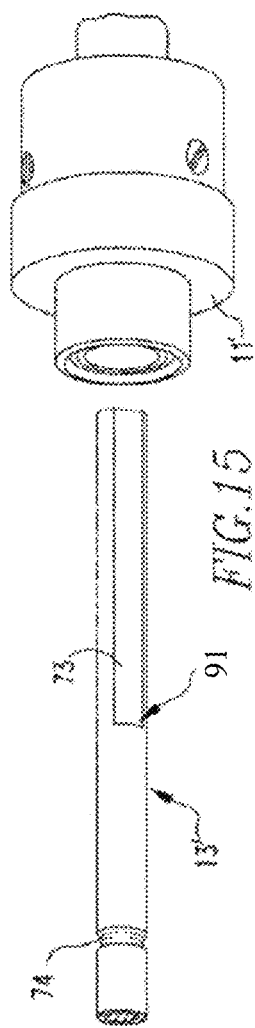

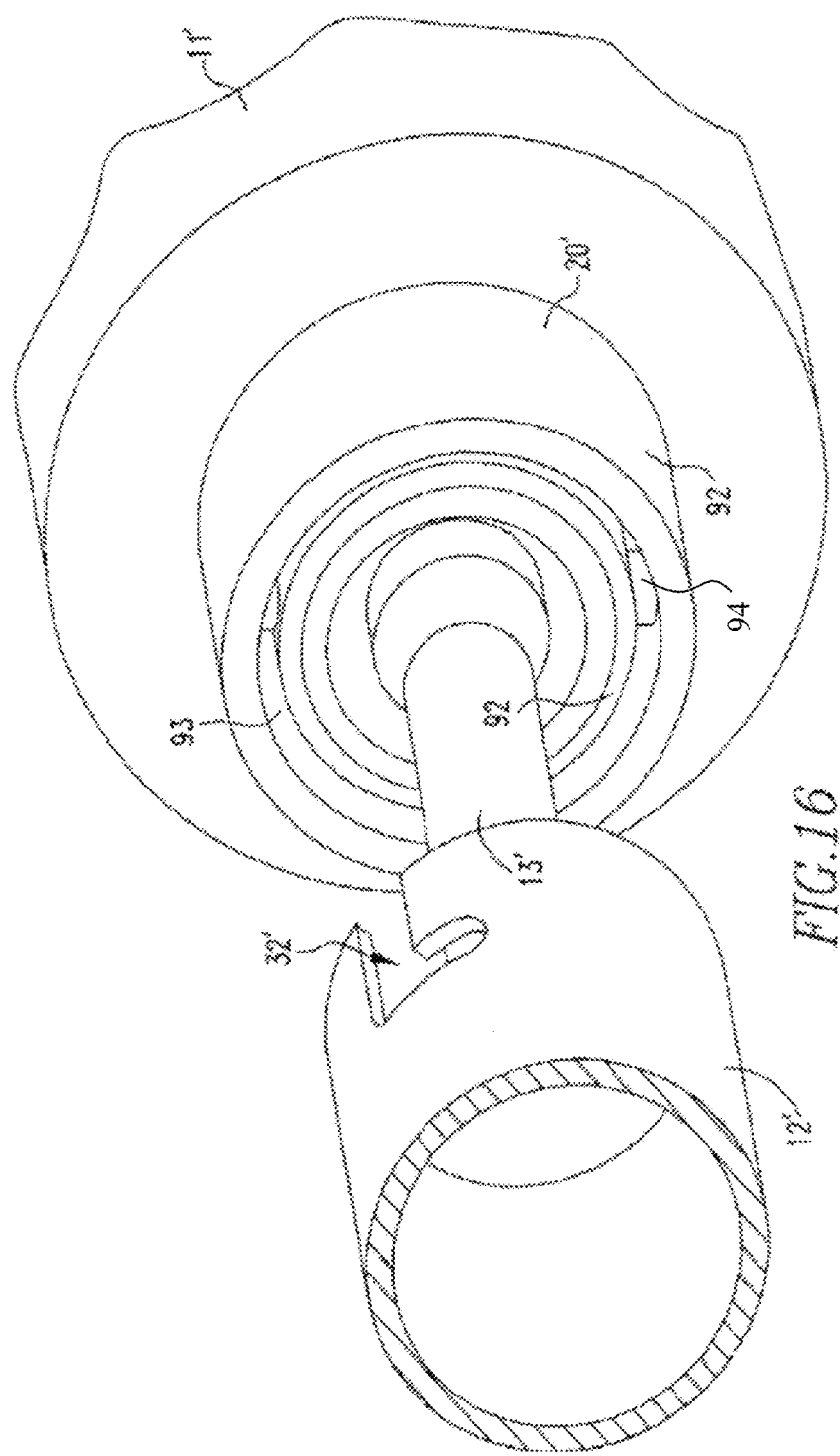

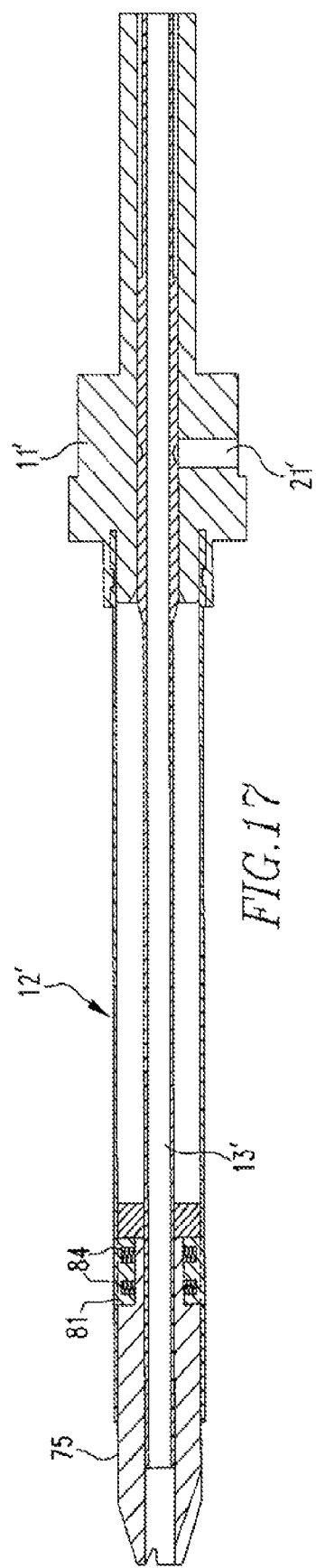

TREPHINE

RELATED APPLICATIONS

This application is the U.S. National Stage of International Application No. PCT/US12/28803, filed on Mar. 12, 2012, which claims priority to and the full benefit of U.S. Provisional Application Ser. No. 61/451,749, filed Mar. 11, 2011, and U.S. Provisional Application Ser. No. 61/451,751, filed Mar. 11, 2011, the entire contents of which are incorporated herein by reference.

BACKGROUND

The present invention relates to medical apparatuses and procedures in general, and more particularly to medical apparatuses and procedures for reconstructing a ligament.

In many cases, ligaments are torn or ruptured as the result of an accident. Accordingly, various procedures have been developed to repair or replace such damaged ligaments.

For example, in the human knee, the anterior and posterior cruciate ligaments (i.e., the "ACL" and "PCL") extend between the top end of the tibia and the bottom end of the femur. Often, the anterior cruciate ligament (i.e., the ACL) is ruptured or torn as the result of, for example, a sports-related injury. Consequently, various surgical procedures have been developed for reconstructing the ACL.

In many instances, the ACL may be reconstructed by replacing the ruptured ACL with a graft ligament. More particularly, in such a procedure, bone tunnels are generally formed in both the top of the tibia and the bottom of the femur, with one end of the graft ligament being positioned in the femoral tunnel and the other end of the graft ligament being positioned in the tibial tunnel, and with the intermediate portion of the graft ligament spanning the distance between the bottom of the femur and the top of the tibia. The two ends of the graft ligament are anchored in their respective bone tunnels in various ways well known in the art so that the graft ligament extends between the bottom end of the femur and the top end of the tibia in substantially the same way, and with substantially the same function, as the original ACL. This graft ligament then cooperates with the surrounding anatomical structures so as to restore substantially normal function to the knee.

Various approaches for anchoring the two ends of the graft ligament in the femoral and tibial bone tunnels are known.

In a known procedure, the end of the graft ligament is placed in the bone tunnel, and then the graft ligament is fixed in place using a headless orthopedic screw, or interference screw. With this approach, the end of the graft ligament is placed in the bone tunnel and then the interference screw is advanced into the bone tunnel so that the interference screw extends parallel to the bone tunnel and simultaneously engages both the graft ligament and the side wall of the bone tunnel. In this arrangement, the interference screw essentially drives the graft ligament laterally, into engagement with the opposing side wall of the bone tunnel, whereby to secure the graft ligament to the host bone with a so-called "interference fit". Thereafter, over time (e.g., several months), the graft ligament and the host bone grow together at their points of contact so as to provide a strong, natural joinder between the ligament and the bone.

Interference screws have proven to be an effective means for securing a graft ligament in a bone tunnel. However, the interference screw itself generally takes up a substantial amount of space within the bone tunnel, which can limit the extent of contact between the graft ligament and the bone tunnel. This in turn limits the region of bone-to-ligament in-growth, and hence can affect the strength of the joinder. It has been estimated that the typical interference screw obstructs about 50% of the potential bone-to-ligament integration region.

One approach to address this issue is to fabricate the interference screws from bioabsorbable materials, so that the interference screw is absorbed over time and bone-to-ligament in-growth can take place about the entire perimeter of the bone tunnel. In general, this approach has proven clinically successful. However, these absorbable interference screws still suffer from several disadvantages. Clinical evidence suggests that the quality of the bone-to-ligament in-growth is somewhat different than natural bone-to-ligament in-growth, and that the bioabsorbable polymers tend to be replaced by a fibrous mass rather than a well-ordered tissue matrix. Absorption can take a substantial period of time, around three years or so, and during this time, the bone-to-ligament in-growth is still restricted by the presence of the interference screw. In addition, for many patients, absorption is never complete, leaving a substantial foreign mass remaining within the body. This problem is exacerbated somewhat by the fact that absorbable interference screws generally tend to be fairly large in order to provide them with adequate strength, e.g., it is common for an interference screw to have a diameter (i.e., an outer diameter) of 8-12 mm and a length of 20-25 mm.

An alternative approach is disclosed in WO 2008/021474, which describes a composite interference screw for attaching a graft ligament to a bone. The composite interference screw comprises a screw frame for providing the short term strength needed to set the interference screw into position and to hold the graft ligament in position while bone-to-ligament ingrowth occurs, and an ingrowth core for promoting superior bone-to-ligament ingrowth. The screw frame is preferably formed from a bioabsorbable polymer, and the ingrowth core is a bone scaffold structure, also formed from a resorbable polymer, so that the composite interference screw substantially completely disappears from the surgical site over time. The bone scaffold structure may also be an allograft, formed from demineralised bone.

The screw frame includes apertures extending intermediate at least some of the screw threads. Those apertures facilitate contact between the side wall of the bone tunnel and ingrowth core.

It is desirable to utilise an autograft ingrowth core formed from the patient's own bone material. As discussed above, cruciate ligament reconstruction and other similar types of reconstructive surgery require a tendon or graft to be inserted in a bone tunnel. Placement of the tunnel is preferably made at the original attachment site of the ruptured ligament or tendon, and is said to be anatomically placed. The tunnel must have a length sufficient to provide appropriate graft engagement for stiffness and strength. When the bone tunnels are formed the drill findings are not generally collected, and are washed away in the drilling process.

In an alternative approach, the core of bone is harvested for future when the bone tunnel is created. Typically, a surgeon will use a coring trephine system to harvest bone from the patient and this will be used to fill the resultant defect to promote healing. Prior to harvesting the bone, a guide wire is drilled through the bone along the proposed path which the bone tunnel will take. The coring trephine system is cannulated and is slid over the guide wire prior to over-drill the path followed by the guide wire.

A particular problem of the above system is that it is difficult to maintain the trephine corer concentrically, relative to the guide wire. This can be overcome by including additional procedural steps as is described in U.S. Pat. No. 5,423,823 which requires the removal of a guide pin after it has been drilled through the tibia. The introduction of a collared guide pin, and subsequent use of a cannulated core saw. Other systems require additional devices to stabilise the coring reamer while drilling.

However, these systems and methods require additional steps (and devices) to control the trephine while drilling, and thus increase the complexity and time required to carry out the procedure Accordingly, there exists a need for a better arthroscopic approach.

SUMMARY

In its broadest sense the present invention provides a trephine comprising an adaptor, a reamer, and a reamer support stem.

According to an aspect of the present invention there is provided a trephine comprising an adaptor, an elongate reamer coupled thereto, and a reamer support stem, wherein the reamer support stem is mounted concentrically within the reamer and adaptor, and wherein at least a portion of the reamer support stem is slidably moveable about a longitudinal axis of the trephine.

Preferably, the reamer support stem is cannulated. More preferably, the reamer support stem is cannulated and permits a guide wire to be received therein. This allows the trephine to be slidably mounted over a guide wire which has been drilled into bone. As a result, the trephine can be used to harvest bone by directly engaging the guide wire, and without the need for additional guides.

Preferably, the reamer is demountably coupled to the adaptor.

Suitably, the reamer support stem and adaptor include complementary engagement means for coupling the reamer support stem to the adaptor. Preferably, the complementary engagement means disengage and allow the reamer support stem to slide proximally through the adaptor when a suitable axial force is applied at the distal end of the reamer support stem. Alternatively, the reamer support stem and adaptor are coupled by friction-fit. Preferably, the reamer support stem is demountably coupled with the adaptor.

Alternatively, the reamer support stem comprises a shaft and collapsible collar. Preferably, the collapsible collar and shaft include complementary engagement means for coupling the collapsible collar to the shaft. Preferably, the complementary engagement means disengage and allow the collapsible collar to slide proximally over the shaft when a suitable axial force is applied to the distal end of the collapsible collar. Alternatively, the collapsible collar and shaft are coupled by friction-fit. Preferably, the collapsible collar is demountably coupled with the shaft.

A system for forming a bone tunnel and harvesting bone material, wherein the system comprises a trephine as described above and a guide wire.

Suitably, the system comprises a pair of compaction pliers. Preferably, the compaction pliers comprise of a pair of levers pivotally joined at a fulcrum located in a distal region of the levers. Preferably, the compaction pliers comprise a set of jaws at the distal ends of the levers, and a pair of handles proximally of the fulcrum. Preferably, the jaws are formed from a pair of opposed complementary shaped plates.

Suitably, the system further comprises a plunger. The plunger can be used to remove compacted bone from the jaws of the compaction pliers.

A method for forming a bone tunnel and harvesting bone material in arthroscopic ligament reconstruction, the method comprising the steps of:
 i) drilling a guide wire through a bone;
 ii) sliding a trephine, as described above, over the guide wire to engage the bone; and
 iii) reaming a tunnel by advancing the trephine into the bone.

The method wherein the ligament is the anterior cruciate ligament, and the bone is the tibia.

BRIEF DESCRIPTION OF THE DRAWINGS

The above and other aspects of the invention will now be described with reference to the following drawings in which:
FIG. 4 is a side view of the partially assembled trephine;
FIG. 5 is a side view of the assembled trephine of FIG. 1;
FIGS. 6A-C are side, sectional side, and close up sectional views of the assembled trephine of FIG. 1;
FIG. 7 is a sectional isometric view of the adaptor in the assembled trephine of FIG. 1;
FIGS. 8A-E are isometric views illustrating the use of the trephine of FIG. 1;
FIG. 14 is a close-up side view of the collar assembly and distal end of the reamer of the trephine of FIG. 10;
FIG. 15 is a close-up isometric view, from a first side, of the adaptor and proximal end of the reamer support stem of the trephine of FIG. 10;
FIG. 16 is a close-up isometric view, from a first side, of the assembled adaptor and reamer support stem of FIG. 14;
FIG. 17 is a section side view of the assembled trephine of FIG. 10;

DETAILED DESCRIPTION

Figure 1:
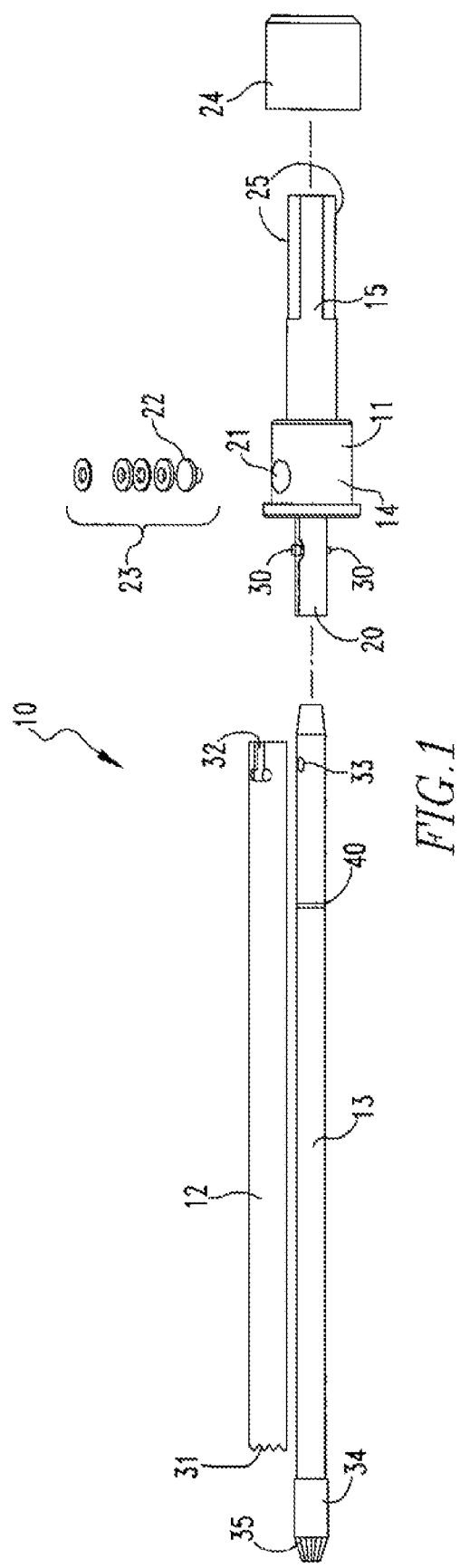
FIG. 1 is an exploded side view of a trephine according to a first embodiment of the invention.

Referring to FIGS. 1 to 5, there is shown an exploded view of a trephine 10 in accordance with one embodiment of the present invention. Trephine 10 is formed of an adaptor 11, a reamer 12 and a reamer support stem 13, each including an internal cannulation.

The adaptor 11 includes a body 14 interposed between a proximal leg 15 and distal head portion 20. Body 14 includes a channel 21 which extends between the outer surface of the adaptor and its internal cannulation. A plunger 22 is moveable within the channel 21, and at least a portion of the plunger extends into the internal cannulation of the adaptor.

A series of spring washers 23 act to bias the plunger towards the cannulation in an assembled configuration with an external collar or cap 24 fitted to body 14. This arrangement will be described in greater detail below with reference to FIG. 6C. Adaptor leg 15 includes flattened regions 25 towards its proximal end which enable the trephine to be connected to a drill (not shown). Distal head 20 includes a pair of opposed radially extending pins 30.

Reamer 12 is formed from a cylindrical tubular member which has an internal diameter that is greater than the external diameter of distal head 20, of adaptor 11. This allows the reamer 12 to be slid onto the adaptor head 20 in an assembled configuration, as discussed with reference to FIGS. 4 and 5 below. Reamer 12 includes a series of bone engaging blades or teeth 31 at a distal end, and a pair of opposed adaptor pin-engaging grooves 32, at a proximal end. The grooves 32 are generally t-shaped, and allow the reamer to be locked on to the adaptor 11 in a bayonet-type arrangement. Although, the pin and groove arrangement are described as a pair of opposed complementary pins and grooves, other suitable arrangements comprising 3, 4 or more complementary pins and grooves could also be incorporated.

Figure 2:
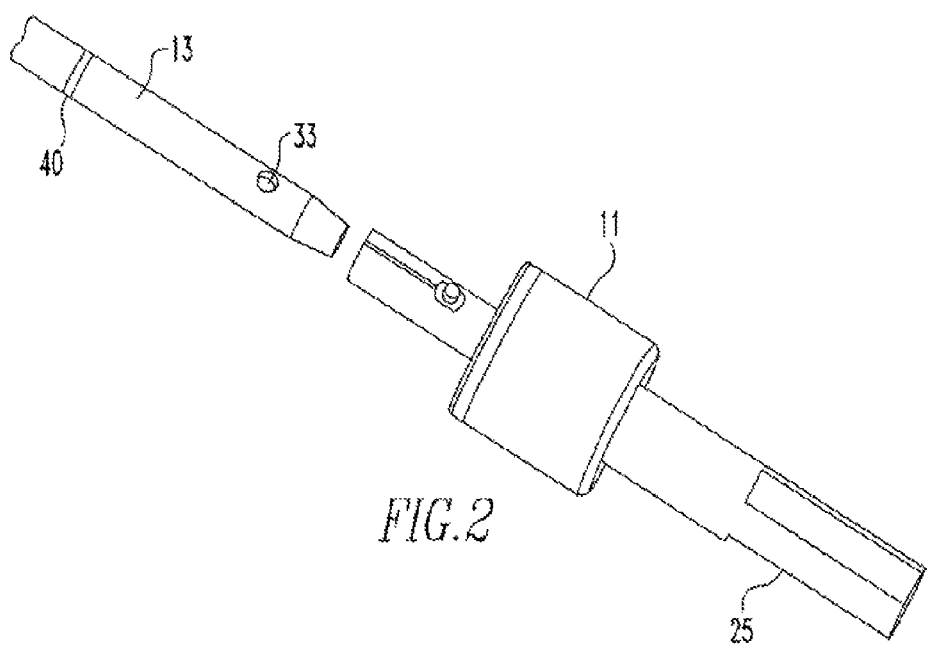
FIG. 2 is a close-up side view of the adaptor and distal end reamer support stem of the embodiment of FIG. 1.
Figure 3:
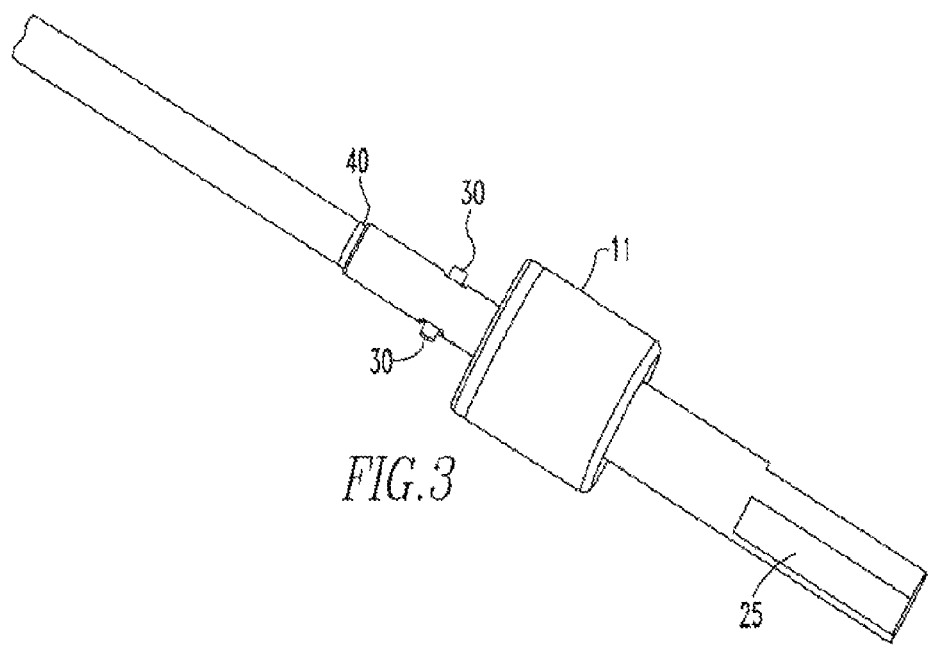
FIG. 3 is a close-up side view of the adaptor and reamer support stem of the embodiment of FIG. 1 in an assembled configuration.

Reamer support stem 13 is formed from a cylindrical tubular member and has an external diameter that is less than the internal diameter of distal head 20, of adaptor 11. This enables the proximal end of the support stem 13 to be slid into distal head 20 of adaptor 11 (FIGS. 2 and 3). The proximal end of support stem 13 includes a tapered conical end which helps to facilitate its insertion into adaptor 11. The distal end of support stem 13 includes a slightly enlarged head 34, which itself includes bone-engaging teeth 35. The proximal region of the support stem 13 includes an aperture 33 which extends between the outer surface and the internal cannulation of the support stem 13. When the support stem is slid into adaptor 11, the portion of plunger 22 which extends into the internal cannulation of the adaptor engages with and extends into aperture 33 of support stem 13 to lock the adaptor 11 and support stem 13 together. A circumferential mark 40 is located in or on the outer surface of support stem 13, in a proximal region and distally of aperture 33.

FIGS. 2 and 3 show detailed views of adaptor 11 and the distal end of reamer support stem 13 as the two components of the trephine are engaged with one another. To aid engagement of aperture 33 of support stem 13 with plunger 22 of adaptor 11, laser mark 40 is provided so that the user knows how far to insert support stem 13.

In FIGS. 4 and 5, the final stage of assembly of trephine 10 is shown. Here, the reamer 12, which will generally be disposable, is slid onto support stem 13. Distal pin-engaging grooves of reamer 12 are lined up with pins 30 of adaptor 11, and the reamer is locked in position on the pins 30 with a small turn.

FIGS. 6 and 7 illustrate the mechanism of engagement of reamer support stem and adaptor 11 in more detail. As shown, plunger 22 is biased towards reamer support stem 13 by spring washers 23 engages with aperture 33 of the support stem. In use of the trephine, as will be described in greater detail below, when a sufficiently large force is applied to the distal end of the support stem this will overcome the engagement of plunger 22 with aperture 33 and cause the support stem to advance proximally relative to the rest of the trephine. It will be recognised that the spring washers can be replaced with a spring or other suitable biasing means.

Referring now to FIGS. 8A-C, use of a trephine system according to the invention is described. The trephine system includes a trephine to core out the bone tunnel, compaction pliers to help cut and shape the harvested bone (see FIG. 9 and relevant description below), and instrumentation to aid in backfilling the bone in the centre of the an interference screw such as that described above, with reference to WO 2008/021474. The trephine system includes a variety of different sized reamers and reamer support stems to accommodate the range of tunnel sizes required for ligament reconstruction procedures.

The first step in the procedure is to insert a guide wire into the tibia, for example, along a path which the tibial tunnel will take (FIG. 8A). This is achieved using an external drill guide (not shown). In a typical procedure to repair a damaged anterior cruciate ligament, a guide wire having a diameter of 2.4 mm will generally be used. Next, the surgeon will select an appropriately sized trephine adaptor, reamer support stem, and reamer that matches to the diameter of the particular graft that will be used. The diameter size for the adaptor, reamer support stem, and reamer should be the same. The reamer support stem is then advanced into the adaptor, which seats properly in the adaptor when the circumferential laser mark on the support stem is flush with the distal end of the adaptor, and plunger 22 has engaged aperture 33 (FIG. 6C). The reamer is subsequently slid over the support stem and secured in place through the locking engagement of pins 30 and grooves 32, and the fully assembled trephine is attached to a drill through the adaptor leg (not shown).

Figure 8D:
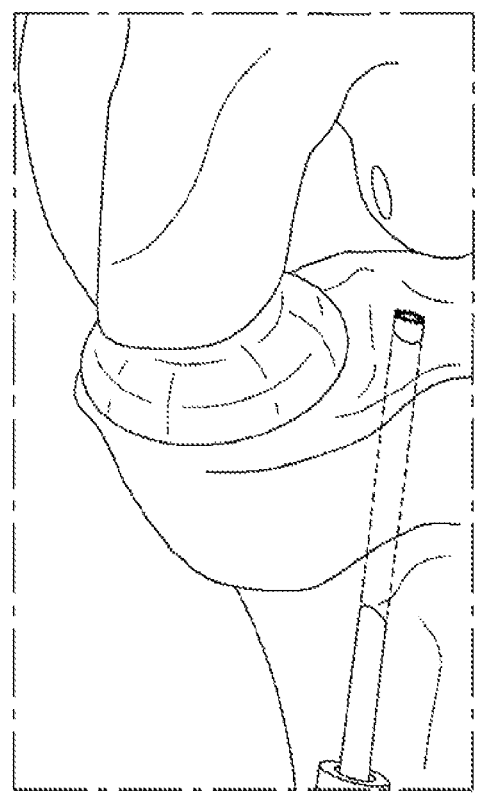

The trephine assembly is then advanced over the guide wire until teeth 35 at the distal end of the reamer support stem engage bone at the point where the guide wire 41 enters the tibia. Further advancement of the trephine assembly initially causes the support stem to drill into the bone a short distance, until teeth 31 of reamer 12 engage with the bone. After which, the force required to advance the reamer becomes sufficient to dislodge plunger 22, located within the adaptor body 14, from within aperture 33 and the support stem 13 moves proximally through the adaptor body and stops advancing as the reamer progresses through the tibia. The reamer is advanced until its distal end fully breaches both tibial cortices and any soft tissue remnants on the tibial plateau (FIG. 8D). This step ensures that the bone harvested within the trephine system can be removed easily from the tibial tunnel.

Figure 8E:
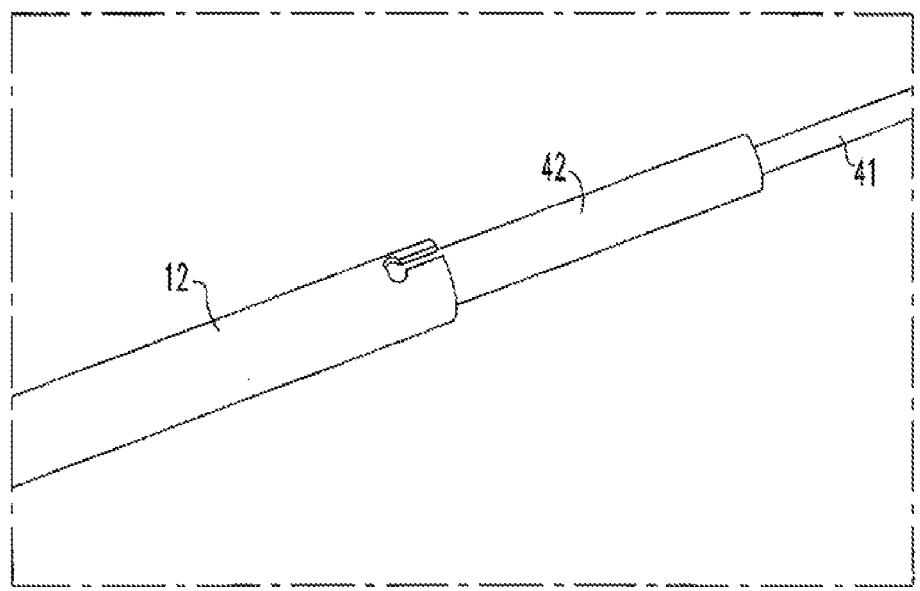

The harvested bone from the trephine system is removed by first disengaging the adaptor and reamer support stem from the guide wire 41. The reamer is then removed from the guide wire 41 and bone plug 42 so that the harvested bone plug 42 exits the proximal, non-cutting, end of the reamer as shown in FIG. 8E. The harvested bone can be used to fill defects in, for example, patellar, tibia, and femoral harvest sites to promote healing.

Figure 9A:
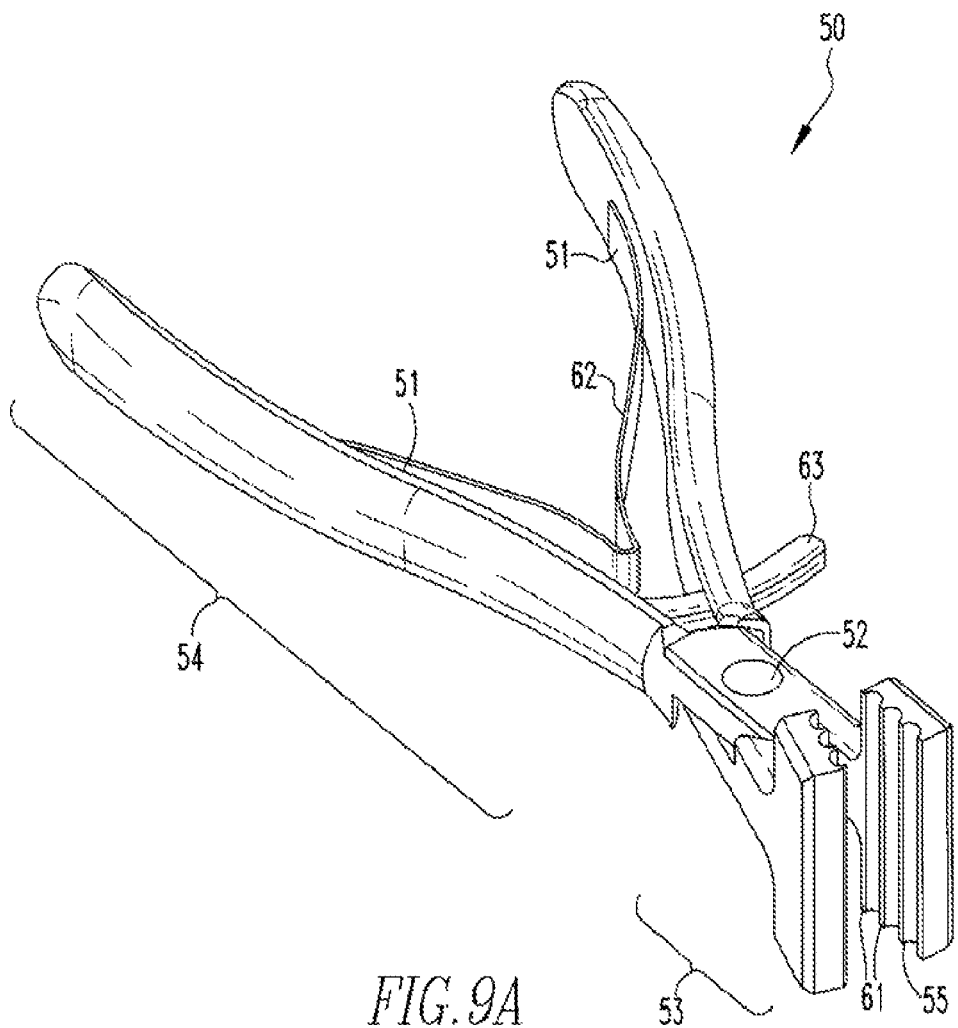
FIGS. 9A-C are isometric views of a set of compaction pliers for use with the trephine of FIG. 1.
Figure 9B:
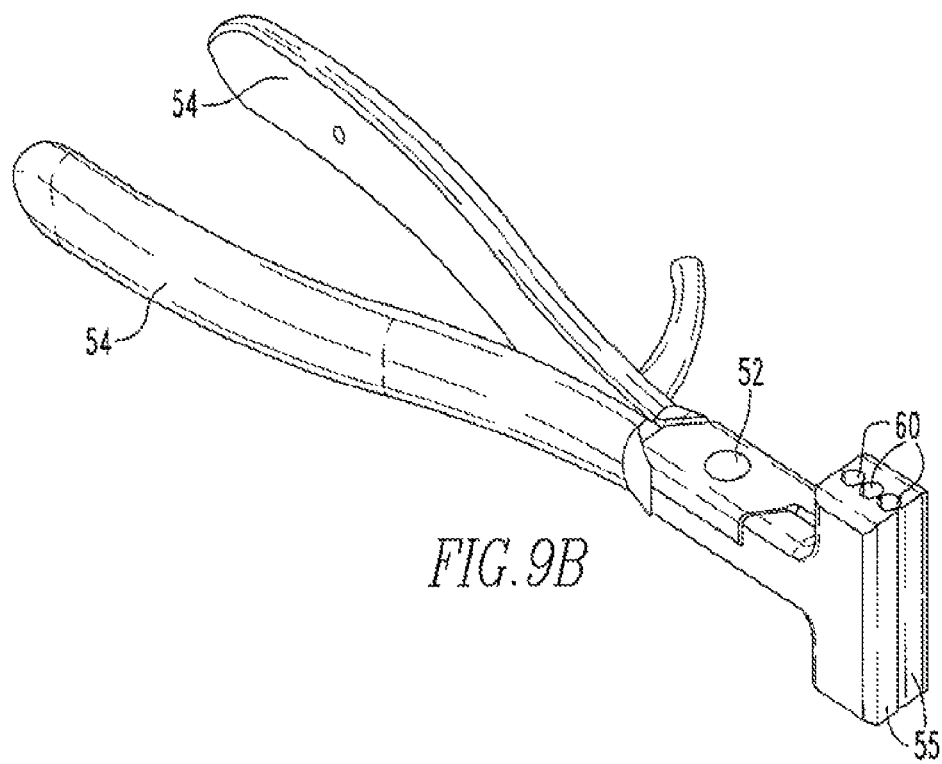
Figure 9C:
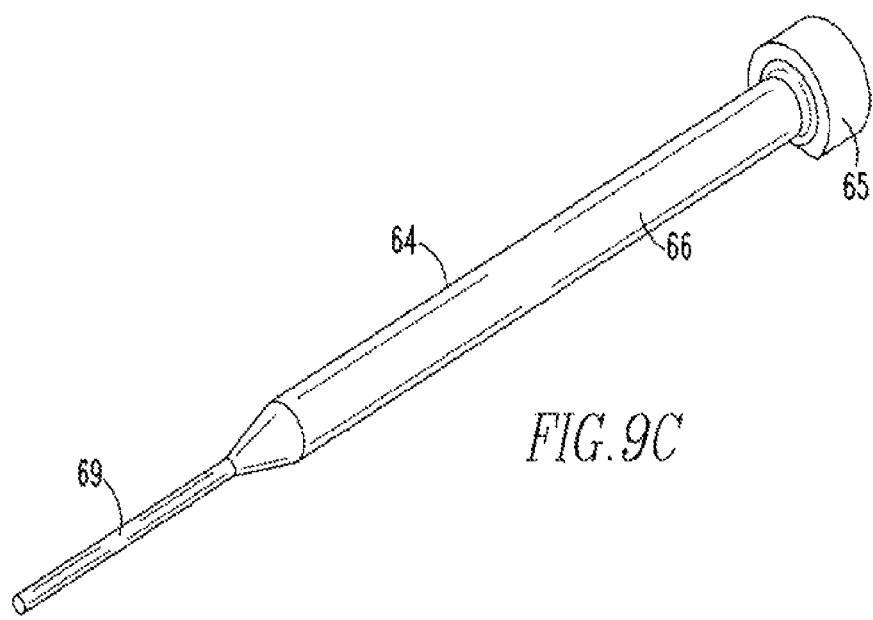

In the case where the bone plug will be used in conjunction with the interference screw of WO 2008/021474, a set of compaction pliers will be required to cut the bone from the guide wire and to shape a suitable bone plug, as will be described. Referring now to FIGS. 9A-C, there is shown a set of medical pliers 50 for cutting and compacting bone. Pliers 50 consist of a pair of levers 51 pivotally joined at a fulcrum located in a distal region of the levers. A set of jaws 53 are provided at the distal ends of levers 51, and the region proximal of fulcrum 52 defines a pair of handles 54. This arrangement creates a mechanical advantage, allowing the force of a user's hand grip to be amplified and focused on an object held within jaws 53. The pliers 50 can be used to manipulate and cut objects too small to be handled with the fingers.

Jaws 53 are formed from a pair of opposed complementary shaped plates 55. As is more clearly shown in FIG. 9B, when shaped plates 55 are brought together, by the user gripping handles 54, a series of cylindrical voids 60 are formed. Accordingly, when, for example, bone tissue is placed between the jaws 53, and plates 55, and pressure is applied to handles 54, the bone tissue is compacted into cylindrical voids 60 to form cylindrical plugs of bone tissue. Edges 61 of shaped plates 55 may be sharpened to aid formation of the cylindrical bone plugs and cut them from any associated bone tissue which may remain within jaws 53 of pliers 50. In the illustrated embodiment, shaped plates includes a series of three complementary grooves which form three cylindrical voids 60, when jaws 53 are brought together. Each of the grooves have a different radius, which will provide three cylindrical bone plugs each having a different diameter. In alternative embodiments, not shown, each of the grooves have an identical radius, which will provide three identical cylindrical bone plugs.

Handles 54 also include biasing means in the form of a spring 62, to bias handles 54, and thus jaws 53, in an open configuration, and a thumb-operated latch to lock the handles and jaws in a desired position.

A plunger tool 64 (FIG. 9C) is also provided for use with pliers 50, to aid removal of cylindrical bone plugs, as will be described in greater detail below. Plunger 64 includes a flat proximal head 65, elongate body 66 and distal pin 69. Pin 69 has a diameter which corresponds to at least one of the cylindrical voids 60 formed by the closed plates 55 of pliers 50.

Figure 10A:
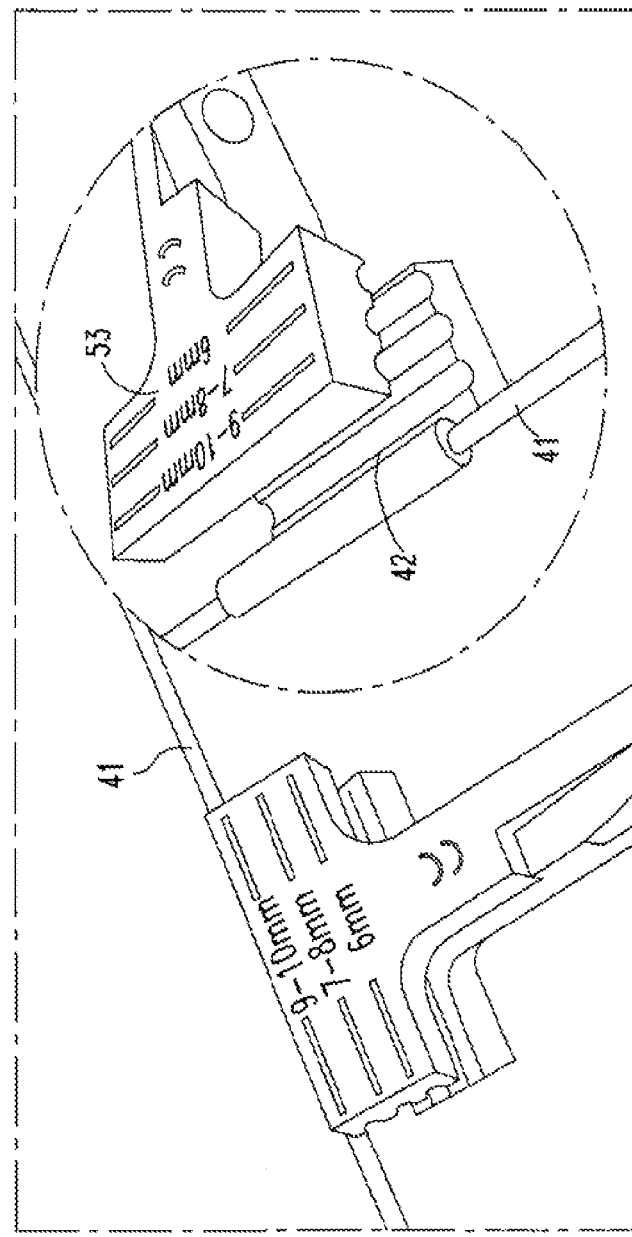
FIGS. 10A-B are isometric views illustrating the use of the compaction pliers of FIG. 9A.

The medical pliers illustrated in FIGS. 9A-C, and described above, can be used in conjunction with the trephine system described herein. At the stage where the harvested bone is removed from the trephine system, still attached on guide wire 41 (FIG. 8E), medical pliers 50 can be used to remove the harvested bone from guide wire 41, as shown in FIG. 10A. The open jaws 53 are placed around and grip the harvested bone plug 42 as it is slid off guide wire 41. Additional pressure is then applied to plier handles 54 to shape the bone plug using the cutting edges of shaped plates 53 to reduce its size. The cylindrical voids 60 in the closed jaws 53 of the compaction act to compress and reshape the harvested bone. Next, latch 63 is closed to lock the pliers with the jaws closed in order to prepare for delivery of the bone plug into the aforementioned interference screw at the appropriate time, and once said screw is in position in bone tunnel.

Figure 10B:
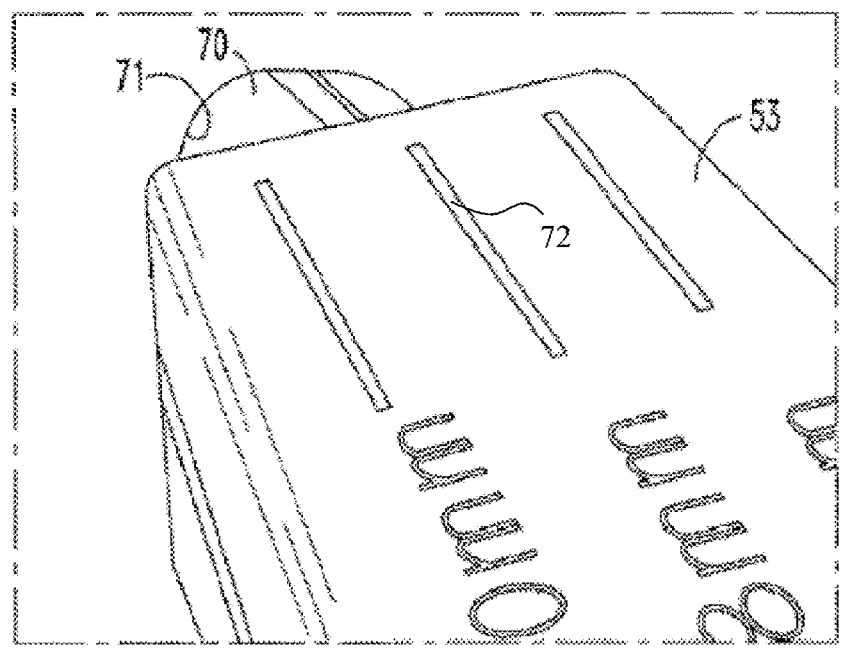

Referring to FIG. 10B, in backfilling the cannulated interference screw 70, located in bone tunnel 71, pliers 50 are positioned directly over the screw by aligning the appropriate size laser mark 72 on jaws 53 to the centre of screw 70. Plunger tool 64 (not shown) in then inserted into the opposite end of the plier jaws and advanced forward to deliver the bone plug into the centre of the screw.

The described system provides an accurate concentric core of bone material by preventing travel of the reamer relative to the guide wire during drilling. The system also allows for the use of fewer devices, and ultimately saves time by allowing the harvesting step to be performed more easily. As discussed above, competitive trephine systems and methods of their use include additional steps or include additional guides to achieve a suitable bone plug. The described system can be used to obtain a bone plug more efficiently, without the need for additional instruments, or requiring additional procedural steps.

An alternative embodiment of a trephine in accordance with the present invention is shown in FIGS. 11 to 17.

Figure 11:
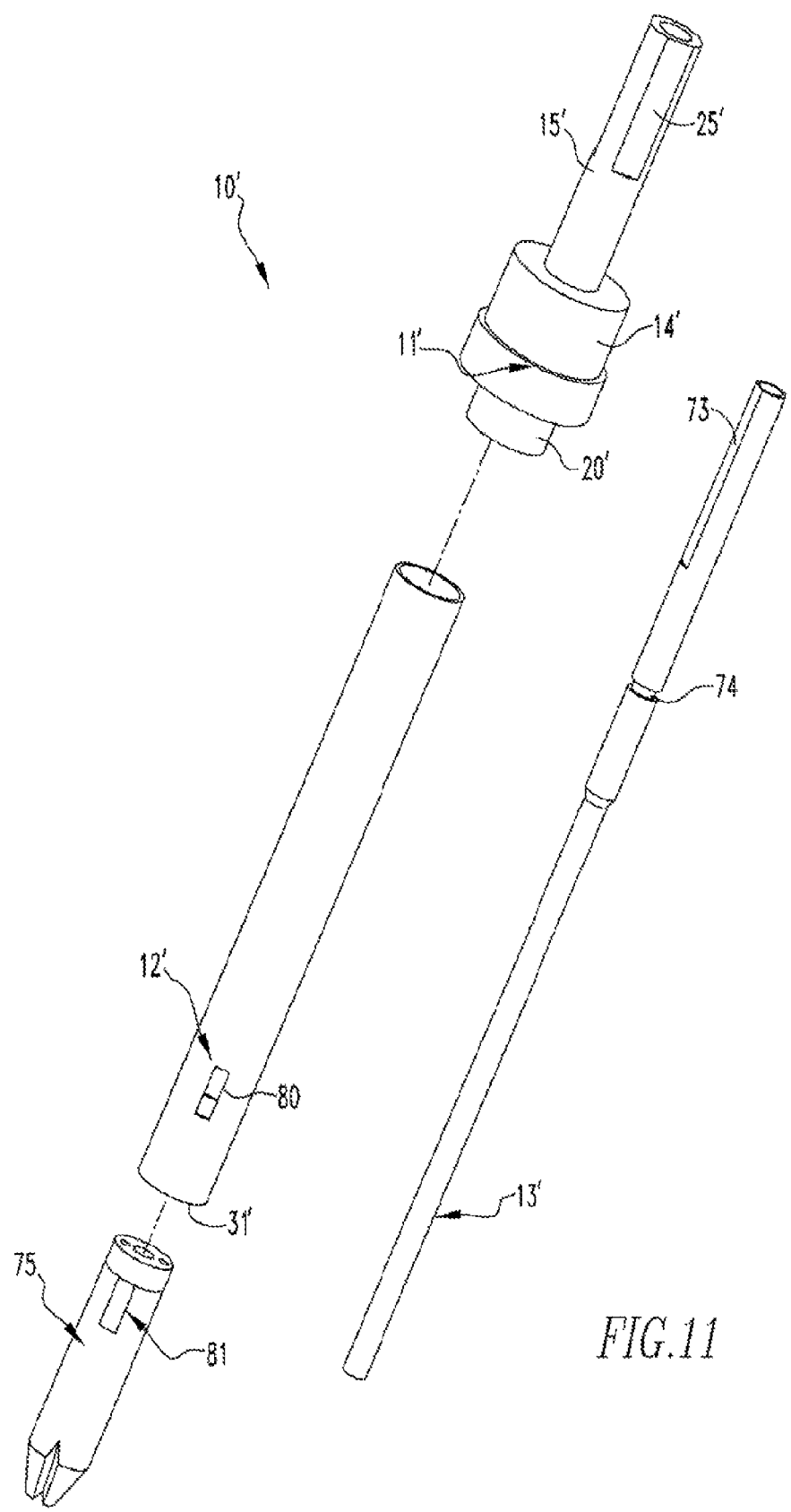
FIG. 11 is an exploded isometric view, from a first side, of a trephine according to a second embodiment of the invention.

According to FIG. 11, there is shown an exploded view of a trephine 10' in accordance with a second embodiment of the present invention. Trephine 10' is formed of an adaptor 11', a reamer 12', a collapsible collar 75 and a reamer support stem 13', each including an internal cannulation.

The adaptor 11' includes a body 14' interposed between a proximal leg 15' and distal head portion 20'. Body 14' includes a channel 21' (FIG. 17) which extends between the outer surface of the adaptor and its internal cannulation. A plunger or pin (not shown) is moveable within the channel 21', and at least a portion of the plunger extends into the internal cannulation of the adaptor. The plunger is biased towards the cannulation with an external collar or cap fitted to body 14'. Adaptor leg 15' includes flattened regions 25' towards its proximal end which enable the trephine to be connected to a drill (not shown). Distal head 20' includes a series of radial grooves for engaging reamer 12' in an assembled configuration. This will be described in greater detail below, with reference to FIG. 16.

Reamer 12' is formed from a cylindrical tubular member, and includes a series of bone engaging blades or teeth 31' at a distal end, and a pair of opposed adaptor pin-engaging grooves 32' (FIG. 16), at a proximal end. The grooves 32' are generally t-shaped, and allow the reamer to be locked on to the adaptor 11' in a bayonet-type arrangement, as will be described below with reference to FIG. 16. The distal region of reamer 12' includes a pair of opposed apertures 80 in the sidewall thereof.

Reamer support stem 13' is formed from a cylindrical tubular member and has an external diameter that is less than the internal diameter of distal head 20', of adaptor 11'. This enables the proximal end of the support stem 13' to be slid into distal head 20' of adaptor 11' (FIG. 15). The proximal end of support stem 13' includes one or more flattened regions 73 which prevent it from rotating independently from the adaptor 11', when assembled and in use. The proximal region of the support stem 13' also includes a circumferential groove 74. When the support stem is slid into adaptor 11', the portion of adaptor plunger which extends into the internal cannulation of the adaptor engages with the circumferential groove 74 to lock the adaptor 11' and support stem 13' together.

Collapsible collar 75 is a cannulated tubular member whose external diameter is less than the internal diameter of reamer 12', and whose internal cannulation has a diameter greater than the external diameter of reamer support stem 13'. Means for engaging reamer 12', in the form of cams plates 81 are located towards the proximal end of collapsible collar 75. The collar 75, is thereby slidable within reamer 12', and slidable on support stem 13'.

Figure 12:
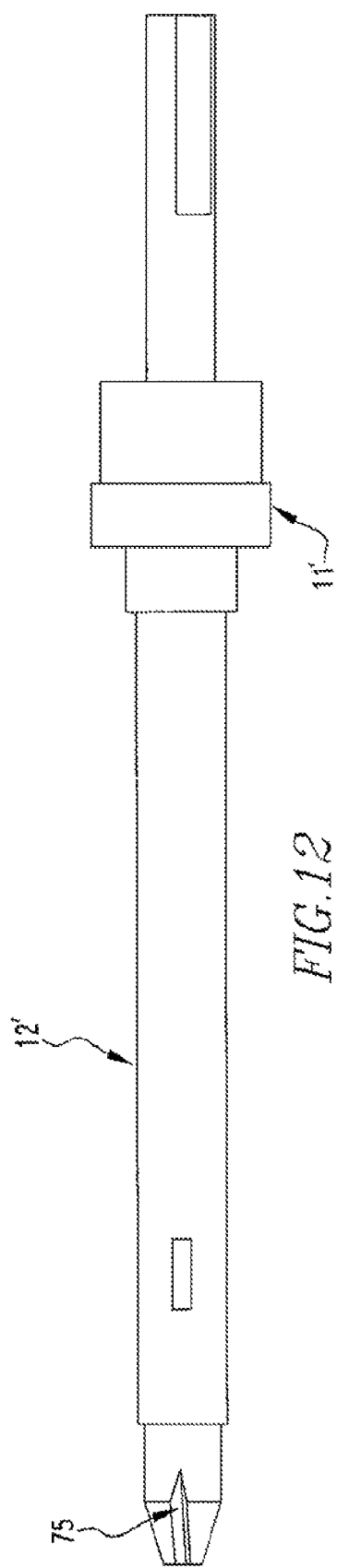
FIG. 12 is a side view of an assembled trephine of FIG. 10.

FIG. 12 shows the fully assembled trephine 10'.

Figure 13:
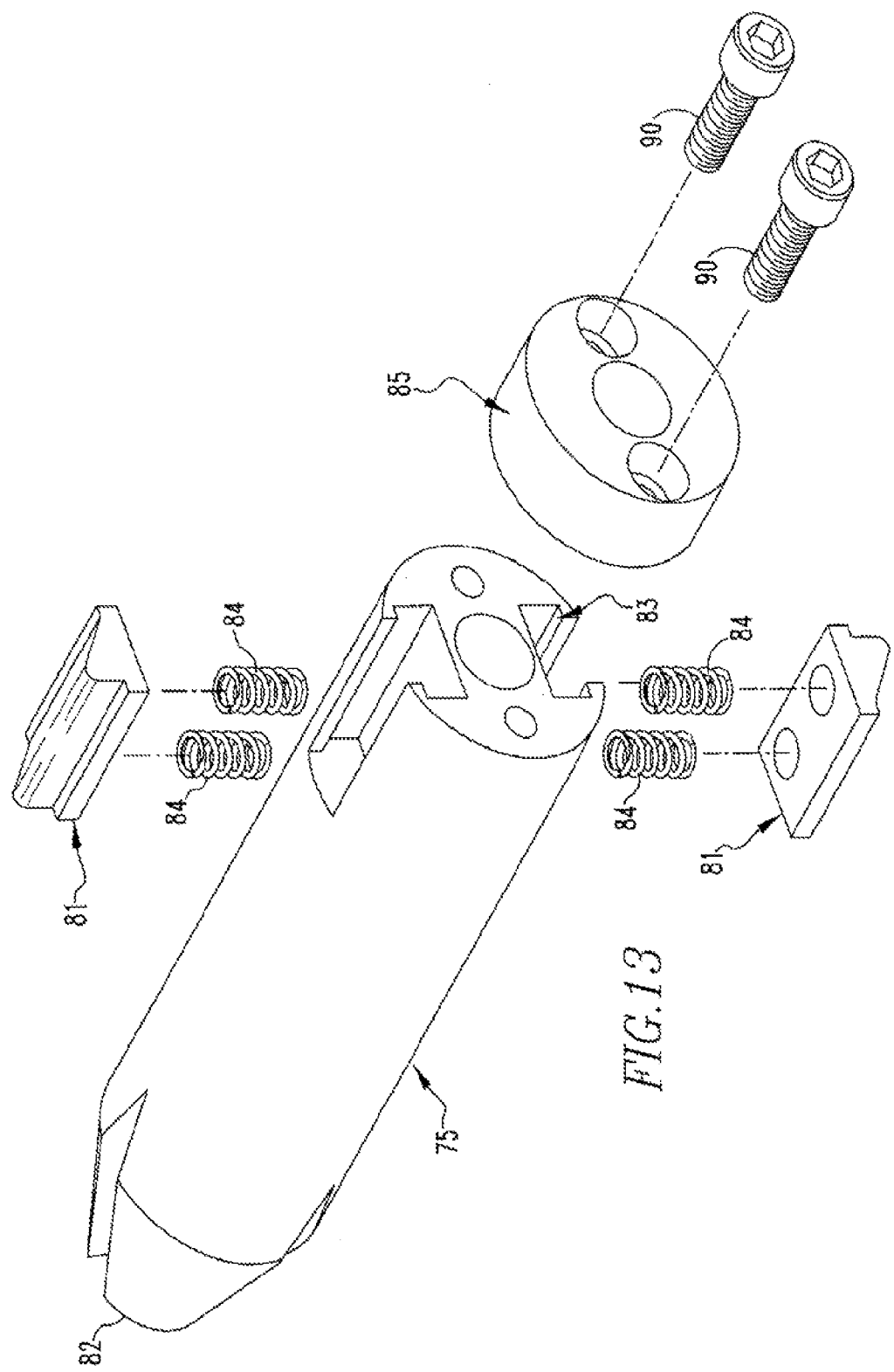
FIG. 13 is an exploded view of the collar assembly of the trephine of FIG. 10.

FIG. 13 shows an exploded view of collapsible collar 75. The collar includes a sharpened distal tip 82, and a pair of rebated slots 83 at its proximal end. Within the rebated slots 83 are housed cams 81 which are outwardly biased by a series of springs 84. A distal collar cap 85 is affixed to collar 75 by means of a pair of screw 90, and prevents cams plates 81 from sliding distally rebated slots 83. The springs enable the cam plates 81 to move within the slots 83.

As shown in FIG. 14, during assembly of the trephine 10', the collapsible collar 75 is loaded in reamer 12' by applying pressure to the cam plates 81 and advancing the collar 75 into reamer 12'. Collar 75 locks within reamer 12' through the action of cam plates 81 engaging apertures 80 in the sidewalls of reamer 12', cam plates 81 clicking out of apertures 80. The collapsible collar 75 is designed to lock when the drill to which the trephine 10' is attached is rotated to advance it into bone, and collapse into the reamer 12' when the direction of rotation of the drill is reversed. This allows the reamer to travel over the collar 75 when harvesting bone tissue.

In an alternative arrangement, the cam plates are replaced by ball bearings or spherical cups that are outwardly radially biased by springs (not shown). In such an alternative embodiment the collapsible collar is held in place within the reamer in an analogous manner, but does not include a directional lock as described above. Accordingly, once the collapsible collar experiences a sufficiently large force to overcome its frictional fit within the reamer, as the trephine is being advanced into bone, it will collapse and allow the reamer to travel over the collar whilst harvesting bone tissue.

In the assembly of trephine 10', reamer support stem 13' is able to slide inside and out of the adaptor 11', and the flattened region 73 prevents it from rotating independently from the adaptor 11' (FIG. 15). One or more plungers 21' engage with groove 74 and prevent it from falling out of the adaptor 11'. Additionally, stop edge 91 prevents the support stem 13' from moving through the adaptor 11' during cutting.

Referring to FIG. 16, head 20' of adaptor 11' includes a pair of concentric collars 92, between which lies a radial groove 93. Within radial groove 93 a pair of pins 94 are located, and pin-engaging grooves 32' at the proximal end of reamer 12' slide onto and interlock to engage the reamer and adaptor. The locking pins inside the groove of the adaptor stabilise the reamer when cutting and also prevent the reamer from falling out of the adaptor.

In FIG. 17 there is shown a section through the assembled trephine 10'

The invention claimed is:

1. A trephine comprising an adaptor, an elongate reamer coupled thereto, and a reamer support stem, wherein the reamer support stem is mounted concentrically within the reamer and adaptor, wherein at least a portion of the reamer support stem is slidably moveable about a longitudinal axis of the trephine, and wherein the reamer support stem and adaptor include complementary engagement means for coupling the reamer support stem to the adaptor,
  wherein the complementary engagement means disengage and allow the reamer support stem to slide proximally through the adaptor when a suitable axial force is applied at a distal end of the reamer support stem.

2. A trephine according to claim 1, wherein the reamer support stem is cannulated.

3. A trephine according to claim 2, wherein the reamer support stem is cannulated and permits a guide wire to be received therein.

4. A trephine according to claim 1, wherein the reamer is demountably coupled to the adaptor.

5. A trephine according to claim 1, wherein the reamer support stem comprises a shaft and collapsible collar.

6. A trephine according to claim 5, wherein the collapsible collar and reamer include complementary engagement means for coupling the collapsible collar to the reamer.

7. A trephine according to claim 6, wherein the complementary engagement means disengage and allow the collapsible collar to slide proximally over the shaft when a suitable axial force is applied to a distal end of the collapsible collar.

8. The trephine of claim 7, wherein the complementary engagement means is configured to disengage upon rotation of the collapsible collar relative to the shaft about the longitudinal axis in a first direction, wherein the engagement means is configured to enable rotation of the collapsible collar relative to the shaft about the longitudinal axis in the first direction while inhibiting rotation of the collapsible collar relative to the shaft about the longitudinal axis in a second direction.

9. A trephine according to claim 5, wherein the collapsible collar and reamer are coupled by friction-fit.

10. A system for forming a bone tunnel and harvesting bone material, wherein the system comprises a trephine according to claim 1, and a guide wire.

11. A system according to claim 10, further comprising a plunger.

12. A system for forming a bone tunnel and harvesting bone material, wherein the system comprises:
  a trephine comprising an adaptor, an elongate reamer coupled thereto, and a reamer support stem, wherein the reamer support stem is mounted concentrically within the reamer and adaptor, wherein at least a portion of the reamer support stem is slidably moveable about a longitudinal axis of the trephine, and wherein the reamer support stem and adaptor include complementary engagement means for coupling the reamer support stem to the adaptor,
  a guide wire, and
  a pair of compaction pliers.

13. A system according to claim 12, wherein the compaction pliers comprise of a pair of levers pivotally joined at a fulcrum located in a distal region of the levers.

14. A system according to claim 13, wherein the compaction pliers comprise a set of jaws at distal ends of the levers, and a pair of handles proximally of the fulcrum.

15. A system according to claim 14, wherein the jaws are formed from a pair of opposed complementary shaped plates.

16. A method for forming a bone tunnel and harvesting bone material in arthroscopic ligament reconstruction, the method comprises the steps of:
  i) drilling a guide wire through a bone;
  ii) sliding a trephine over the guide wire to engage the bone, the trephine including
    an adaptor, an elongate reamer coupled thereto, and a reamer support stem,
    wherein the reamer support stem is mounted concentrically within the reamer and adaptor,
    wherein at least a portion of the reamer support stem is slidably moveable about a longitudinal axis of the trephine, and
    wherein the reamer support stem and adaptor include complementary engagement means for coupling the reamer support stem to the adaptor, wherein the complementary engagement means disengage and allow the reamer support stem to slide proximally through the adaptor when a suitable axial force is applied at a distal end of the reamer support stem; and
  iii) reaming a tunnel by advancing the trephine into the bone.

17. A method according to claim 16, wherein the ligament reconstruction is anterior cruciate ligament reconstruction, and the bone is a tibia.

18. A trephine comprising an adaptor, an elongate reamer coupled thereto, and a reamer support stem, wherein the reamer support stem is mounted concentrically within the reamer and adaptor, wherein at least a portion of the reamer support stem is slidably moveable about a longitudinal axis of the trephine, and wherein the reamer support stem and adaptor include complementary engagement means for coupling the reamer support stem to the adaptor, wherein the complementary engagement means includes a deflectable plunger mechanism for engagement with an aperture or groove.

\* \* \* \* \*